United States Patent
Asfora

(10) Patent No.: US 8,808,206 B2
(45) Date of Patent: *Aug. 19, 2014

(54) ANALGESIC IMPLANT DEVICE AND SYSTEM

(76) Inventor: Wilson T. Asfora, Sioux Falls, SD (US)

(*) Notice: Subject to any disclaimer, the term of this patent is extended or adjusted under 35 U.S.C. 154(b) by 0 days.

This patent is subject to a terminal disclaimer.

(21) Appl. No.: 13/586,719

(22) Filed: Aug. 15, 2012

(65) Prior Publication Data

US 2013/0066243 A1    Mar. 14, 2013

Related U.S. Application Data

(63) Continuation of application No. 12/326,649, filed on Dec. 2, 2008, now Pat. No. 8,469,908, which is a continuation-in-part of application No. 11/784,376, filed on Apr. 6, 2007, now Pat. No. 8,512,264.

(51) Int. Cl.
*A61H 1/00* (2006.01)
(52) U.S. Cl.
USPC ................................. 601/46; 601/79; 128/898
(58) Field of Classification Search
USPC ............ 601/2, 46.78, 46, 78, 79; 607/3, 9, 40, 607/49, 57; 623/1.11, 1.15, 24; 128/898, 128/899

See application file for complete search history.

(56) References Cited

U.S. PATENT DOCUMENTS

| | | | |
|---|---|---|---|
| 7,670,278 B2* | 3/2010 | Westerkull | 600/25 |
| 2005/0267406 A1* | 12/2005 | Hassler, Jr. | 604/96.01 |
| 2006/0247719 A1* | 11/2006 | Maschino et al. | 607/40 |
| 2007/0203533 A1* | 8/2007 | Goren et al. | 601/46 |

* cited by examiner

*Primary Examiner* — Quang D Thanh
(74) *Attorney, Agent, or Firm* — Kokka & Backus, PC

(57) ABSTRACT

Techniques associated with an implant system for imparting vibratory massage to tissue within a body is disclosed. Methods include placing an implant device near a surface of a stomach, the implant device configured to produce and communicate a vibration to stomach tissue, the implant device including a case forming a portion of an exterior of the implant device and defining an interior of the implant device, a vibration generator mounted on the case to vibrate the implant device, and a tissue engaging structure located on the exterior surface of the case to engage the stomach tissue, securing the implant device to the stomach, and activating the vibration generator of the implant device to cause the implant device to vibrate against the stomach, wherein the vibration stimulates a nerve to suppress an appetite.

11 Claims, 32 Drawing Sheets

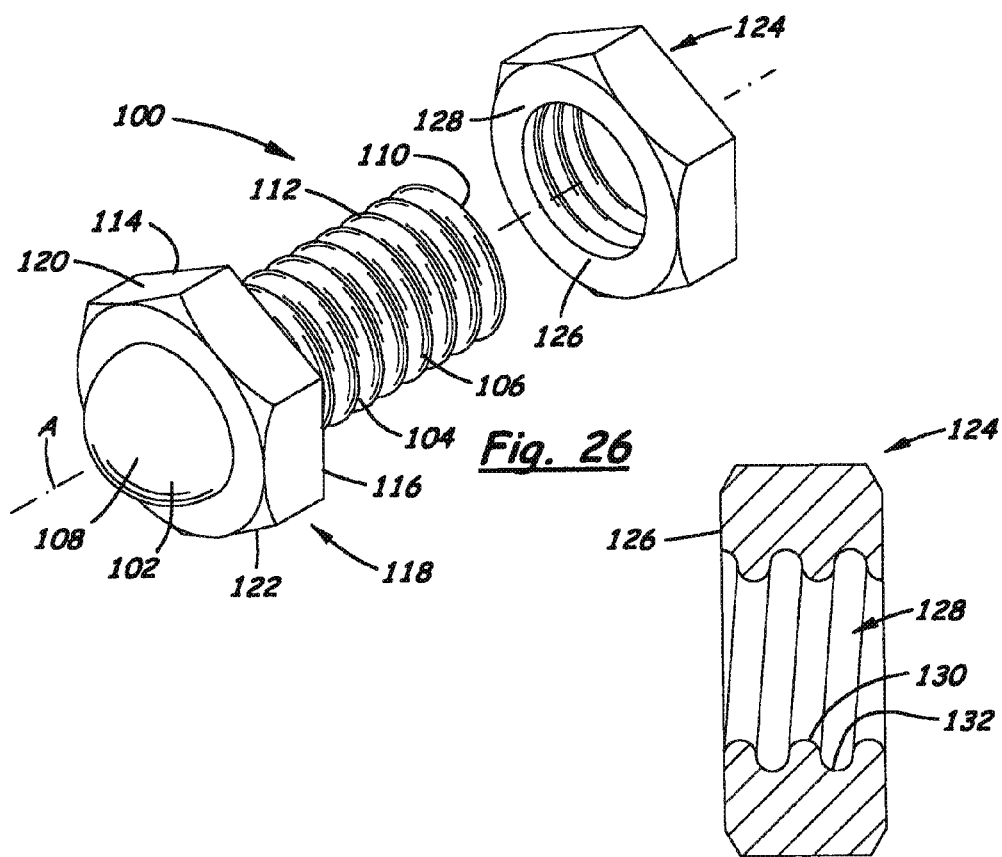
Fig. 26
Fig. 27
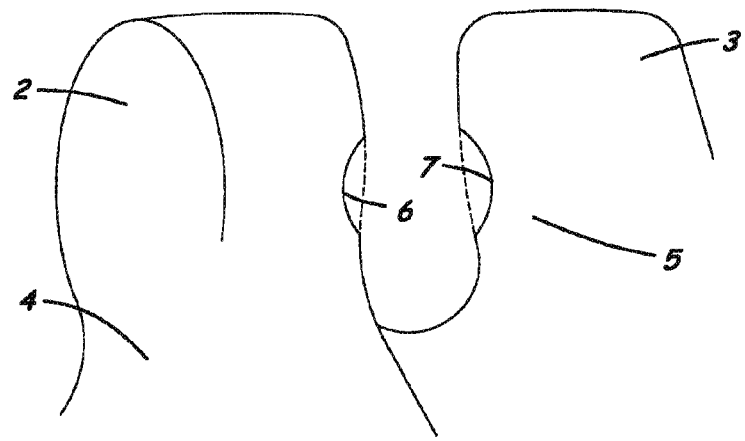
Fig. 28

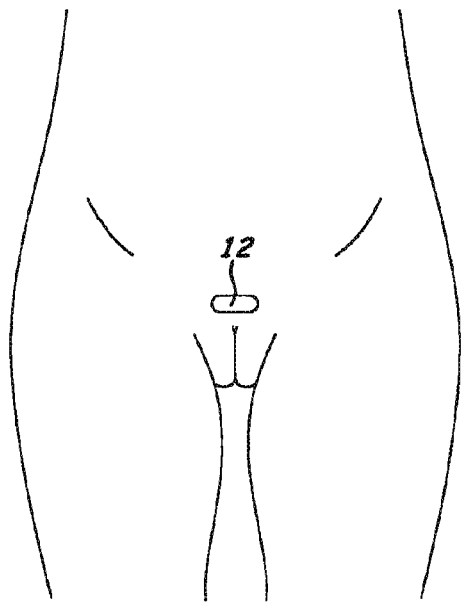
Fig. 40
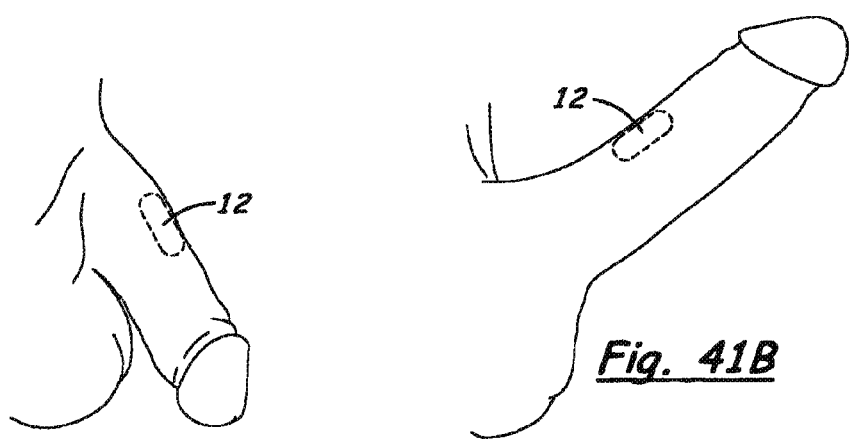
Fig. 41A
Fig. 41B

ANALGESIC IMPLANT DEVICE AND SYSTEM

CROSS-REFERENCE TO RELATED APPLICATIONS

This application is a continuation of U.S. patent application Ser. No. 12/326,649, filed Dec. 2, 2008, now U.S. Pat. No. 8,469,908 which is a continuation-in-part of U.S. patent application Ser. No. 11/784,376, filed Apr. 6, 2007, now U.S. Pat. No. 8,512,264 and is related to co-pending U.S. patent application Ser. No. 13/586,742, filed Aug. 15, 2012, entitled "Analgesic Implant Device and System," and U.S. patent application Ser. No. 13/586,795, filed Aug. 15, 2012, entitled "Analgesic Implant Device and System," and U.S. patent application Ser. No. 13/586,807, filed Aug. 15, 2012, entitled "Analgesic Implant Device and System," all of which are incorporated by reference herein in their entirety for all purposes.

FIELD

The present invention relates to pain relief, and more particularly to an analgesic implant device and system.

BACKGROUND

The analgesic effects of kinetic remedies such as vibratory massage are well known in the medical field. Vibratory stimulation of muscle and other bodily tissue has been a proven medical therapy for many years. One problem facing many people suffering from pain is that a kinetic remedy can rarely be readily administered at the first signs of discomfort. Many of the causes of pain can be significantly relieved or reduced if treatment is administered during the early onset of pain. Further, using known equipment and techniques it can be difficult to apply vibratory stimulation to the affected area for long periods of time, or at least as long as the pain may persist, and thus may only provide a temporary relief.

Another problem facing pain sufferers is that the source of the pain may develop in an area of the body that is not readily or effectively accessible by known vibratory massage devices. In many cases the source of the symptom is buried too deep within the body for an external vibratory massage device to have any significant effect without irritating the intervening tissue. In other cases the source of the symptom may be too close to other sensitive tissue that would be adversely affected by an external vibratory stimulus strong enough to be effective on the tissue that is the source of the pain. In yet other cases the source of the pain is isolated from the effects of an external kinetic remedy by bone or other tissue that may dampen or otherwise attenuate the vibratory effect.

For example, some have proposed instruments employed for the removal of intervertebral implants that use ultrasonic vibrations to loosen and dislodge the prosthesis from the adjoining bone. This instrument is used during a surgical process, and is not believed to be suitable for applying useful vibrational massage to tissue for any length of time.

Others have proposed devices that employ ultrasonic vibrational energy in place of electrical stimulus for cardiac pacing, cardioversion, and defibrillation in response to detected arrhythmia. Such devices do not appear to be designed to provide vibrations with amplitude that is capable of providing pain relief. Further, these devices apply the vibrations to the heart or lungs, and some of the device even appear to employ vibrational elements located inside one of the ventricles of the heart, and thus is not suggestive of something that could provide pain relief.

Still others have proposed device that apply vibrations to the exterior of the body for various purposes. For example, systems have been devised for translating feelings or sensations from a prosthetic limb to the residual limb using acoustic vibrations, and is not designed or intended for therapeutic pain relief.

Yet others have proposed devices that are implanted in the body but are only caused to vibrate by stimulus applied from outside the body, such as when an acoustic transducer located outside of the body focuses energy on the implanted device. Thus, the implanted device is not able to generate vibrations by itself without the external stimulus being applied.

Further, devices have been proposed for implantation for the purpose of hearing assistance, audiological support, or replacement and testing. Although many of these devices include a vibratory element, the purpose of the vibratory generation is to pass on acoustic stimulation to sensory organs and is not believed to be suitable for vibratory massage.

Therefore what is needed is a device that has the ability to administer vibratory stimulus to the source of pain in a direct manner so as to administer the vibratory massage in a targeted manner to the tissue of a patient with the least amount of collateral effect, and has the ability to apply the vibratory massage at the earliest signs of the occurrence of the pain.

SUMMARY

To meet these needs, the present invention generally provides a medically implanted device that can be positioned proximate to the source of pain and is capable of administering a vibratory massage using a relatively low amount of force necessary to remedy the pain without adversely affecting the surrounding tissue.

In one aspect of the invention, an analgesic implant system is disclosed for imparting vibratory massage to tissue of a patient from within the body of the patient.

The system comprises an implant device configured to produce and communicate a vibration to body tissue located adjacent to the implant device. The implant device may include a case forming at least a portion of an exterior of the implant device and defining an interior of the implant device, and a vibration generator configured to vibrate the at least a portion of the exterior of the implant device. The device may further include a power supply configured to supply power to the vibration generator and a switch configured to selectively permit power from the power supply to be supplied to the vibration generator. The implant device may still further include a power receiver configured to receive electrical energy from a location external to the body of the patient when the implant device is implanted within the body of the patient and a signal receiver configured to receive signals from a location external to the body of the patient when the receiver is located in the body of the patient, with the signal receiver being in communication with the switch to actuate the switch.

In another aspect of the invention, a method of imparting vibratory massage to tissue of a body of a patient is disclosed, and may comprise providing an implant device, identifying tissue within the body of the patient as a source of discomfort, implanting the implant device within the body of the patient, and causing vibration of the implant device within the body of the patient to thereby vibrate the identified tissue.

In yet another aspect of the invention, an analgesic implant system is disclosed for imparting vibratory massage to tissue of a patient from within the body of the patient. The system comprises an implant device configured to produce and communicate a vibration to bone tissue of the body of the patient. The implant device includes a case forming at least a portion of an exterior of the implant device and defining an interior of the implant device, with the case having an exterior surface having an elongated shape with a longitudinal axis and a first end and a second end. The implant device further includes a vibration generator mounted on the case and configured to vibrate the at least a portion of the exterior of the implant device. The implant device also includes a tissue engaging structure located on the exterior surface of the case and configured to secure the case on the bone tissue of the body of the patient.

In still another aspect of the invention, a method of suppressing appetite in a patient is disclosed. The method comprises providing an implant device configured to produce and communicate a vibration to tissue of the body of the patient, and the implant device includes a case forming at least a portion of an exterior of the implant device and defining an interior of the implant device, a vibration generator mounted on the case and configured to vibrate the at least a portion of the exterior of the implant device, and a tissue engaging structure located on the exterior surface of the case and configured to secure the case on the tissue of the body of the patient. The method further comprises securing the implant device to an exterior surface of the stomach of the patient, and activating the vibration generator of the implant device to cause the implant device to vibrate against the exterior surface of the stomach.

In yet still another aspect of the invention, a method of inducing urination by a patient is disclosed. The method comprises providing an implant device configured to produce and communicate a vibration to tissue of the body of the patient, and the implant device includes a case forming at least a portion of an exterior of the implant device and defining an interior of the implant device, a vibration generator mounted on the case and configured to vibrate the at least a portion of the exterior of the implant device, and a tissue engaging structure located on the exterior surface of the case and configured to secure the case on the tissue of the body of the patient. The method further includes securing the implant device to an exterior surface of the bladder of the patient, and activating the vibration generator of the implant device to cause the implant device to vibrate against the exterior surface of the bladder.

In another aspect of the invention, a method of inducing a bowel movement by a patient is disclosed. The method comprises providing an implant device configured to produce and communicate a vibration to tissue of the body of the patient, with the implant device including a case forming at least a portion of an exterior of the implant device and defining an interior of the implant device, a vibration generator mounted on the case and configured to vibrate the at least a portion of the exterior of the implant device, and a tissue engaging structure located on the exterior surface of the case and configured to secure the case on the tissue of the body of the patient. The method further includes securing the implant device to an exterior surface of the colon of the patient, and activating the vibration generator of the implant device to cause the implant device to vibrate against the exterior surface of the colon.

A significant benefit provided by the present invention is that vibratory massage may be applied in a more direct manner to internal tissue that may not normally be effectively treated by vibration massage applied to the exterior of the body of the patent. Also, the vibration may be applied without significantly limiting the activities of the patient while the massage is being applied. Further, the massage may be applied more quickly when a pain condition arises, and may be continued as long as the pain condition persists, again without the massage otherwise limiting the activities of the patient.

Further advantages of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive manner in which there are illustrated embodiments of the invention.

BRIEF DESCRIPTION OF THE DRAWINGS

Various embodiments or examples of the invention are disclosed in the following detailed description and the accompanying drawings:

FIG. 9 is a schematic side cross sectional view of the implant device of

FIG. 8 in accordance with an embodiment of the present invention;

FIG. 26 is a schematic perspective view of an alternative implant device according to an embodiment of the present invention;

FIG. 27 is a schematic sectional view of a bearing member of the implant device of FIG. 26 in accordance with an embodiment of the present invention;

FIG. 28 is a schematic side view of a pair of spinous processes located on adjacent vertebrae of the spine, particularly illustrating preparation of the processes for mounting the implant device of FIG. 26;

FIG. 40 is a schematic illustration of a different alternative implant device positioned in the pelvic region of a female in accordance with an embodiment of the present invention;

FIG. 41A is a schematic illustration of yet a different alternative implant device positioned in a flaccid penis, with the implant device being shown in broken lines, in accordance with an embodiment of the present invention; and FIG. 41B is a schematic illustration of still a different alternative implant device positioned in an erect penis, with the implant device being shown in broken lines, in accordance with an embodiment of the present invention.

DETAILED DESCRIPTION

In the following detailed description, reference is made to the accompanying drawings which form a part hereof, and in which is shown by way of illustration specific embodiments in which the invention may be practiced. These embodiments are described in detail sufficient to enable those skilled in the art to practice the invention, and it is to be understood that other embodiments may be utilized and that structural, logical and mechanical changes may be made without departing from the spirit and scope of the present invention. The following detailed description is, therefore, not to be taken in a limiting sense, and the scope of the present invention is defined by the appended claims.

Figure 1:
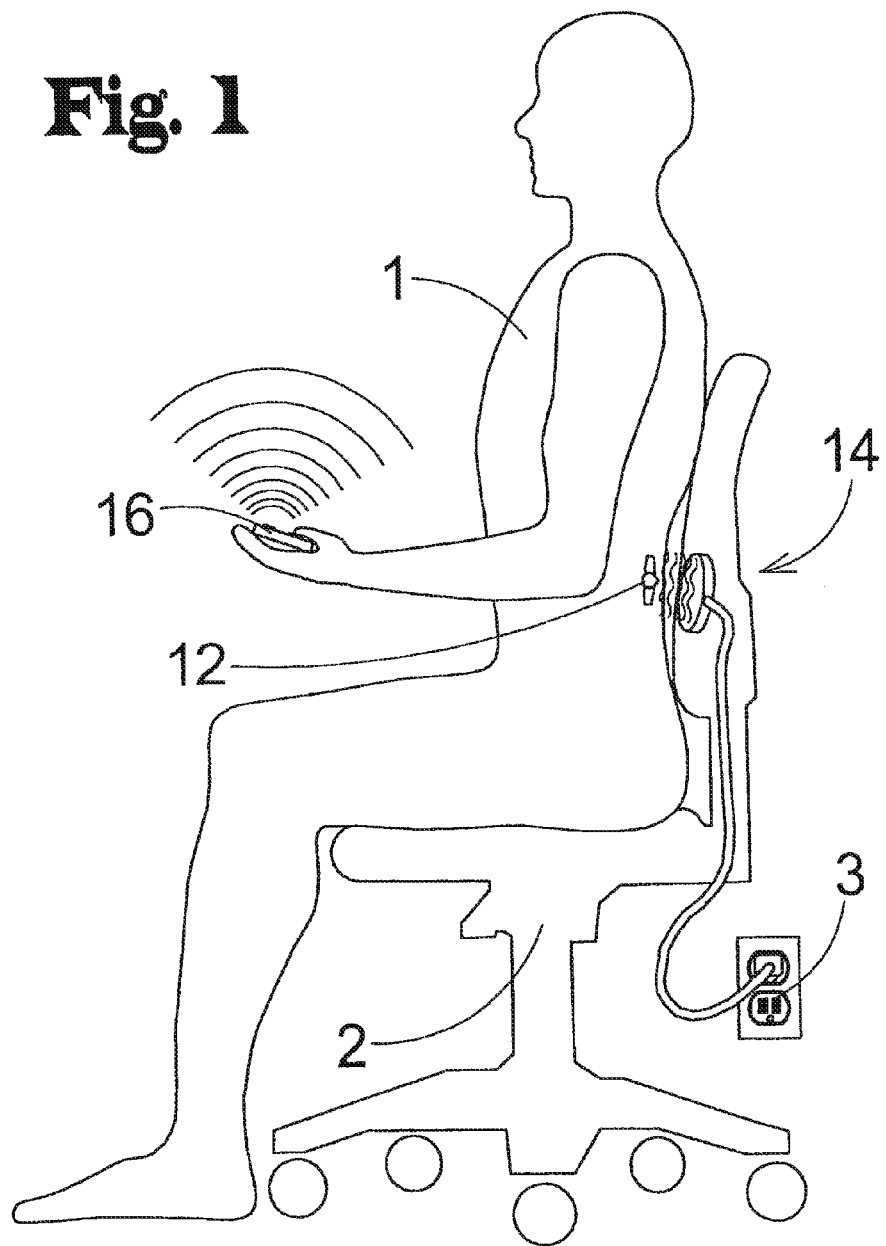
FIG. 1 is a schematic side view of a patient illustrating various parts of the system in accordance with the present invention.

FIG. 1 depicts one embodiment of the apparatus of the analgesic implant system (10) which includes an implant device (12), a charging system (14) and a remote control device (16). As shown in greater detail in FIG. 2, the charging system (14) may include an inductive transmitting coil (88) that may be positioned in relatively close proximity to the receiving coil (86) within the implant device (12) to permit recharging of the internal power supply (78) without requiring a wired connection therebetween.

Turning back to FIG. 1, the transmitting coil (88) may be put into electrical communication with a power source (3), which is illustrated as a common electrical outlet but is not so limited. FIG. 1 shows the transmitting coil (88) of the charging system (14) illustratively mounted to a piece of furniture (2), such as the chair depicted, but the invention is not so limited, and other convenient locations such as the mattress pad of a bed, a car seat in a vehicle or even clothing are within the scope of the invention. The transmitting coil (88) may be attached to the outer surface of the chair but it is anticipated that the charging system (14) may be integrated into a piece of furniture (2) so that its presence is less obvious.

To increase the convenience of use of such an implanted device over a prolonged period of time, the implant device (12) may be self-contained with all critical elements contained within the case (20) and may also be hermetically sealed. The wireless remote control device (16) facilitates these characteristics. As a self contained implanted device may have a limited amount of power to operate the implant device, a wireless system for recharging the device is useful so that the internal power supply (78) may be fully integrated into the device (12), and may even be fully contained in, the case (20). The propensity of a vibrating device to shift or even migrate within a subject's body would stipulate that the implant device be mounted to the region to which its function is to be applied. Therefore the device would require various securing methods suitable to the type of tissue within the device's proximity.

The remote control device (16) may be any device that the patient (1) is able to operate and utilize to send wireless signals that are interpretable by the implant device (12) to regulate the function of the implant device (12). The medium of wireless communication may include any frequencies of the electro-magnetic spectrum including radio waves, microwaves, magnetic impulses and the like. The remote control device (16) is illustrated in FIG. 1 in the hand of the patient (1), and may be configured similar to other handheld remote control devices (16) used to control televisions, media devices, car doors, computers, and garage doors, but the invention is not so limited. It is anticipated that the remote control device (16) may be in the form of a cellular phone in communication with a larger communications network (18) (see FIG. 4), and may send signals to the implant device (12) via a central broadcast location. Optionally, the remote control device (16) may be coupled or combined with the transmitting coil (88) to send control input or data to the implant device (12) via information encoded within the energy transmitted by the transmitting coil. In this example the user interface may be coupled to the charging system (14) or the furniture (2) wherein the charging system (14) resides.

The implant device (12) is shown in FIG. 1 surgically implanted into the back of the patient (1). The implant device (12) may be positioned in almost any location within the patient (1), such as locations among the various organs and tissues of the patient (1). It should be recognized that positioning the implant device (12) in different locations may affect the appropriate placement of the transmitting coil (88) of the charging system (14) so that the transmitting coil (88) is located within a functional proximity to the receiving coil (86) of the implant device (12).

Figure 2:
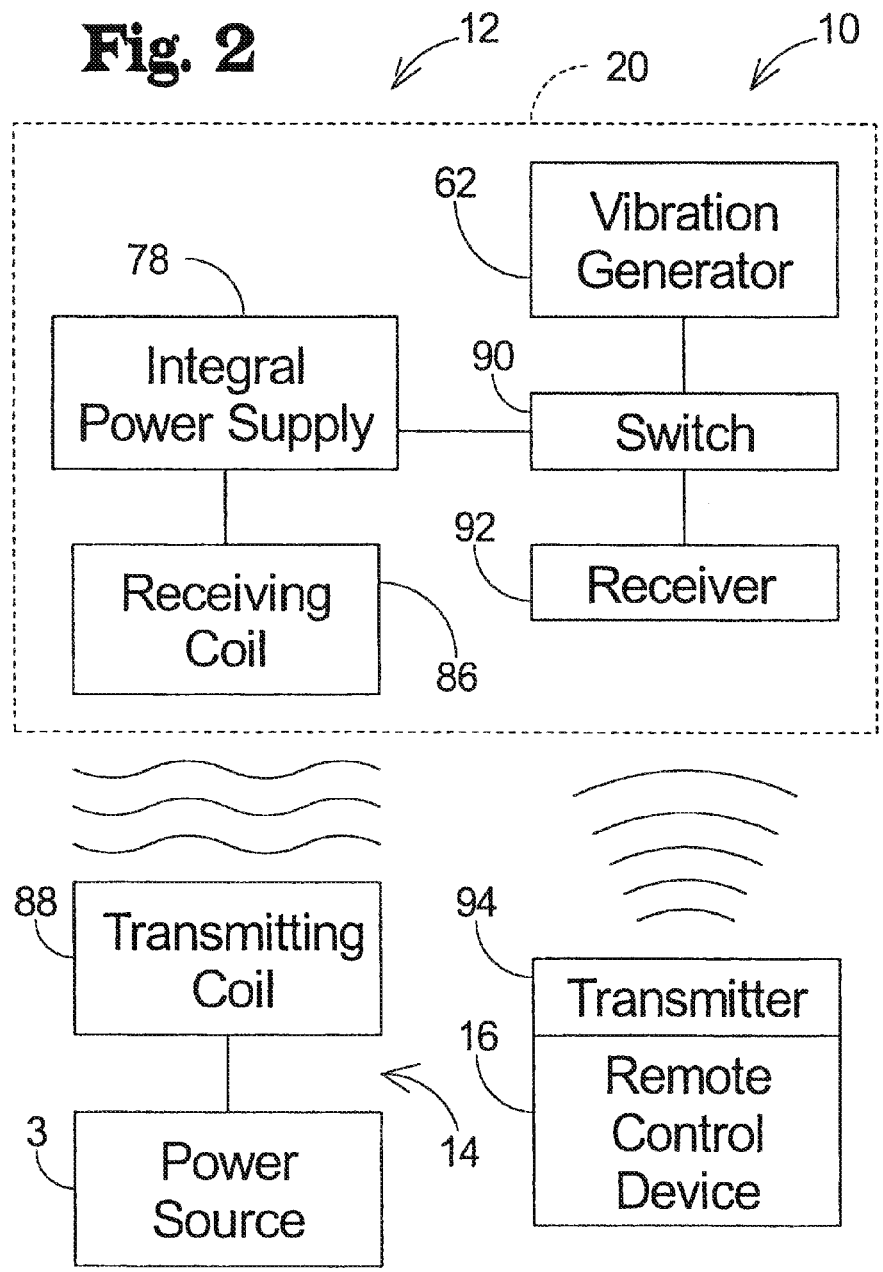
FIG. 2 is a schematic block diagram of an embodiment of the present invention illustrating the functional components and their relationships.

FIG. 2 illustrates a relatively simple embodiment of the operational structure and interaction of the functional elements of the analgesic implant system (10). The power source (3) provides electricity to the transmitting coil (88) that inductively transfers power to the receiving coil (86) located within the case (20) of the implant device (12). This transference of power is represented by the wavy lines between the transmitting coil (88) and the receiving coil (86). The power from the receiving coil (86) is sent to the internal power supply (78) and stored, such as by a rechargeable battery, for later use. Alternately the power could be passed directly to the vibration generator (62) as it is being received by the receiving coil (86). The remote control device (16) may send a signal depicted as radiating curved lines, upon the actuation of a user interface via a transmitter (94) to the receiver (92) that may be located within the case (20) of the implant device (12). The user interface may comprise a button, lever switch, knob, touch pad, touch screen, voice activation system, and the like. The receiver (92) may communicate the signal to a switch (90) that controls the flow of power to the vibration generator (62). The vibration generator (62) may be rigidly attached to the case (20) to cause the case (20) of the implant device (12) to vibrate thus producing mechanical waves to massage the tissue in contact with the case (20) of the implant device (12). The vibration generator (62) may employ a number of different means to produce the vibrations, for example; an electrical motor (64) coupled to a flywheel (70) with an eccentric mass, a piezoelectric vibrator (72), a solenoid (76), a magnetic oscillator (74) and the like. Other methods of producing a vibration are well known to those skilled in the art.

Figure 3:
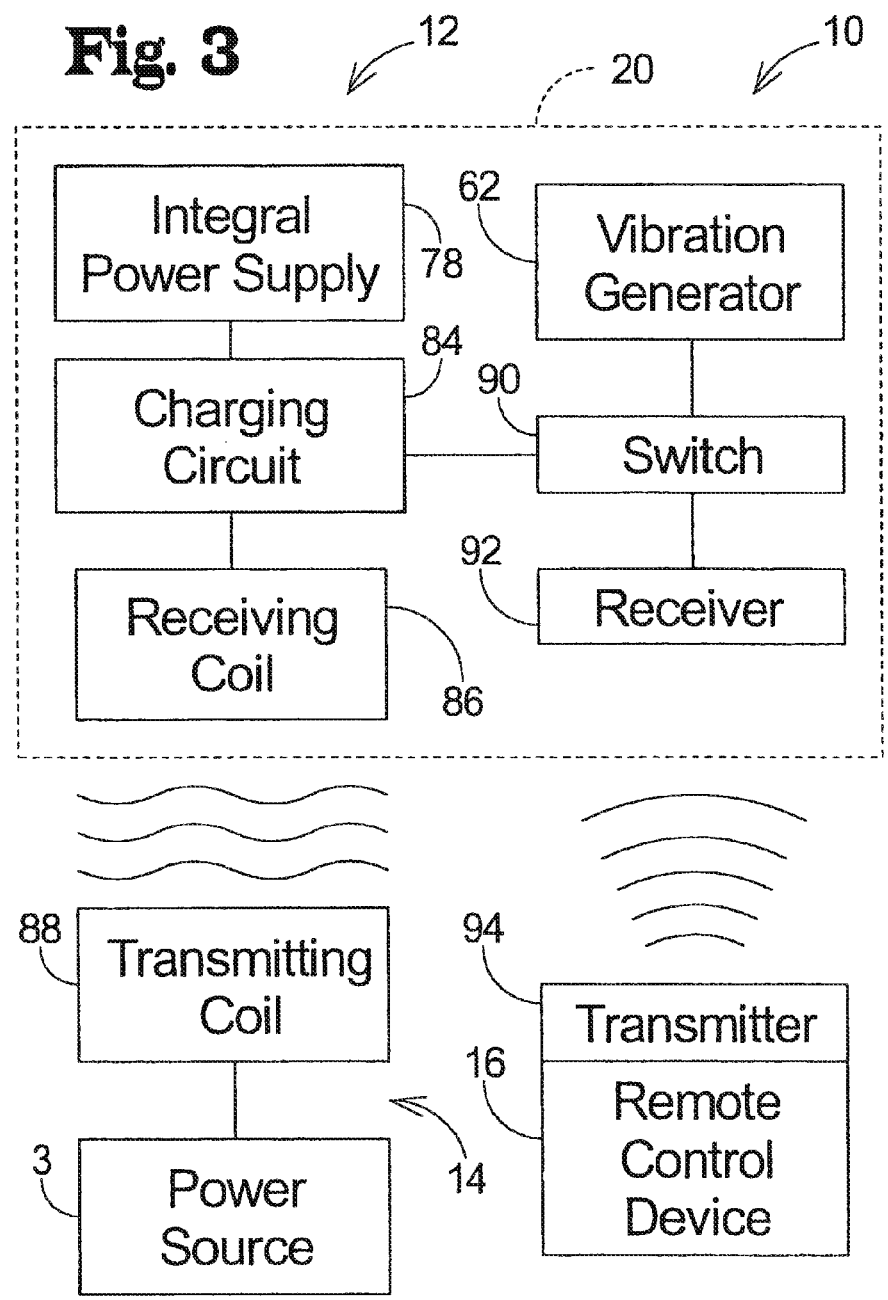
FIG. 3 is a schematic block diagram of another embodiment of the present invention that includes a charging circuit.

FIG. 3 depicts a similar system to the embodiment illustrated in FIG. 2 with the inclusion of a charging circuit (84).

The charging circuit (84) represents one of many types of circuitry that may benefit the function of the implant device (12). A charging circuit (84) may be employed within the implant device (12) to control proper charging and/or discharging of the internal power supply (78), to maintain the life of the internal power supply (78), reduce the possibility or lessen the effect of hydrogen evolution in a rechargeable battery (80) or to monitor and report the status and/or condition of the internal power supply (78), for example, to the patient (1).

Figure 4:
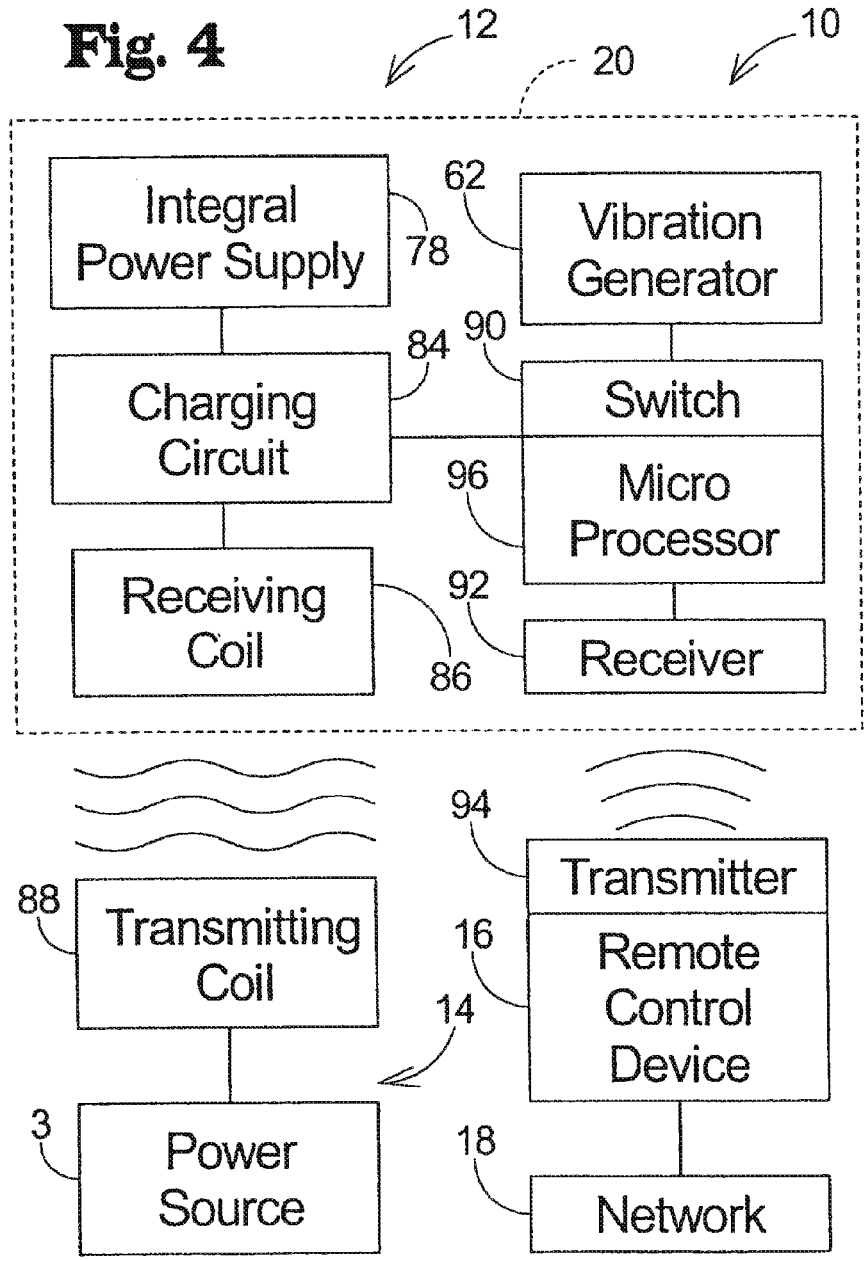
FIG. 4 is a schematic block diagram of yet another embodiment of the present invention that includes a microprocessor.

FIG. 4 depicts the analgesic implant system (10) with additional elements to further expand the functionality of the system (10). The implant device (12) in FIG. 4 includes a micro processor (96) that may provide a plurality of functions through the application of logical processes. Physically the switch (90) may be integrated into the microprocessor (96) but optionally the switch (90) may remain separate. Likewise the charging circuit (84) may be integrated into the micro processor (96) or may be a physically separate element.

The functions of a micro processor (96) within the implant device (12) may be further expanded if the data communicated between the implant device (12) and the remote control (16) is transmitted over a communications network (18) by, for example, for sharing with other entities, such as other people or systems so it is therefore anticipated that the remote control device (16) may be.

In general, the vibration generator (62) causes at least a portion of the case to vibrate with an amplitude sufficient to affect and transmit vibration to adjacent tissue, and at least one, and maybe more than one, frequency that is suitable for providing a massage to the adjacent tissue. In virtually all embodiments of the invention, the frequency or frequencies employed are sub-ultrasonic, and may be in the range of those frequencies below 20 kHz. Other embodiments may employ frequencies below 10 kHz. It is believed that the most useful frequencies are between approximately 1 kHz and 8 kHz, and frequencies within the range of approximately 1400 Hz and 7200 Hz are even more effective, with some of the most effective frequencies occurring between approximately 3240 Hz and 3250 Hz. Of course, the frequency or frequencies employed may depend upon the tissue to be treated, and the type of treatment to be administered.

If an electrical motor (64) is employed as a vibration generator (62) the specific type of motor (64) used may vary depending on the requirements of the implant device (12). Structurally miniature electrical motors (64) are known to those skilled in the art, including disc motor (68) configurations as well as cylindrical motor (66) configurations to facilitate the desired location of the implant device (12) and the requisite effect desired to alleviate or eliminate pain in the patient (1). The operational speed of the motor (64) may be used to control the frequency of the vibrations generated. The frequency of the vibrations employed may be specific to the type of tissue to be affected or optionally the frequency of the vibrations may be selected for the type of the tissue that is desired to remain unaffected by the vibrations during administration of a vibratory massage remedy. The frequency of the vibrations employed may also be affected by the source or specific symptoms of the pain. In some embodiments, a variable speed motor (64) permits the speed of the motor (64) may be controlled to vary the frequency of the massage vibrations produced by the device. In some embodiments, the speed of the motor (64) may be controlled via the switch (90) by controlling the amount of power flowing to the motor (64). Optionally, a microprocessor (96) may control the switch (90) to obtain the frequency or frequencies desired.

Figure 18:
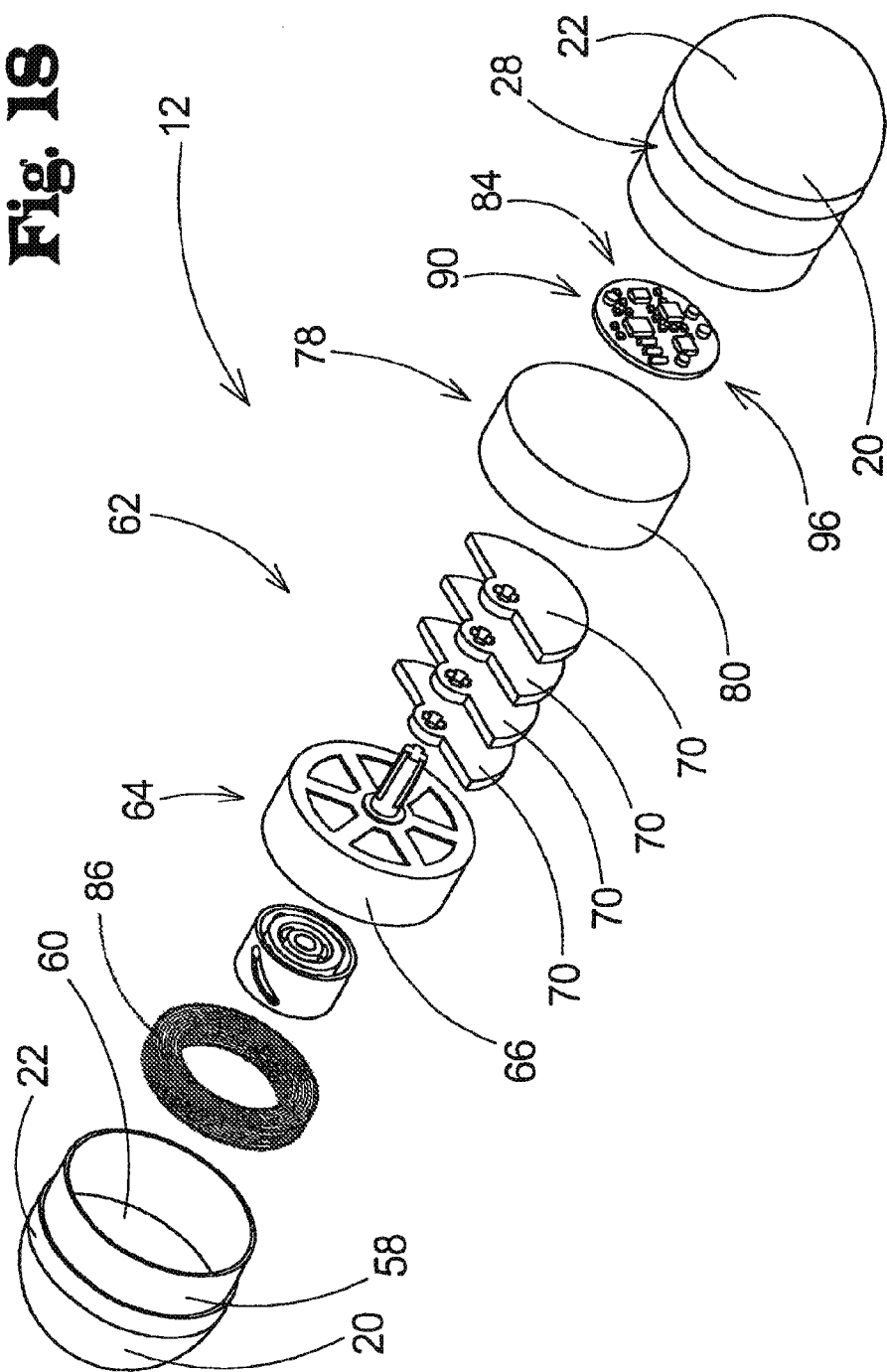
FIG. 18 is a schematic exploded perspective view of yet a different implant device according to an embodiment of the present invention.

In embodiments utilizing an electrical motor (64) as the vibration generator (62), the weight of the eccentrically-mounted mass and the degree of eccentricity from the axis of rotation affects the amplitude of each vibration. The amplitude of the vibrations may be selected based upon the type of tissue to be affected. For example, bone tissue (6) may require a higher degree of amplitude than soft muscle tissue (4) to achieve the desired effect. The amplitude of the vibration may also be selected based upon the proximity of the implant device (12) to the tissue that is the target of the vibratory massage. For example, if the tissue that is the target of the vibratory massage is in direct contact with the implant device (12), the amplitude required may be lower than if the targeted tissue is relatively large in size or if the vibrations need to be communicated through intervening tissue to reach the targeted tissue. Also, the source or specific symptoms of the pain may be most effectively remedied by a vibration of specific amplitude. The magnitude of the mass of a flywheel (70) and/or the degree of eccentricity of the flywheel may dictate the amplitude of the vibration produced by the vibration generator (62). Predefined levels of amplitude may be established by the mechanical structural design of the flywheel (70) during manufacture. Optionally, the magnitude of the mass and/or the degree of the eccentricity (controlled by the placement of the mass on the flywheel (70)) may be varied mechanically. There are a number of ways of mechanically varying the positioning of the mass on the flywheel (70). One such illustrative example is shown in FIG. 18 in which a set of flywheels (70) may engage the shaft or axle of a motor (64) as the motor (64) shifts positions. By varying the collective number and/or position of the flywheels (70), the sum of the eccentric mass can be varied. Each flywheel (70) includes a specific mass that is positioned eccentrically with respect to the axis of the flywheel (70). Through the use of a direct current stepper motor (64) the various weighted sections can be combined in various configurations that change the center of mass to thereby vary the eccentricity. For example, if two flywheel (70) discs are engaged by the motor (64) in a manner such that the masses are opposed at an angle of 180° to each other, the mass of the combined flywheel (70) would be centered upon the axis and the vibration generator (62) would not produce vibrations as there would be no eccentricity. If the two flywheel (70) discs are coupled to each other on the axle with the masses positioned at a 90° angle with respect to each other, the collective center of mass would be located along an axis oriented at an angle between the masses at a smaller diameter from the axis than the actual placement of the masses to produce a medial vibratory amplitude. If the two flywheel (70) discs where coupled to each other on the axle with both masses oriented at the same angle to the axis of the axle, the center of mass would be at the farthest radial distance from the axis of the axle to produce the greatest amount of vibratory amplitude. Many other techniques for mechanically varying mass and eccentricity are known to those skilled in the art.

If a piezoelectric vibrator (72) is employed as a vibration generator (62), a range of frequencies can be achieved electronically by controlling the polarization of the dipole crystal lattice within the ceramic of the piezoelectric vibrator. Piezoelectric vibrators (72) are commonly constructed in arrays or layers of individual piezoelectric ceramic wafers, and by increasing or decreasing the number of individual wafers, layers or sections of an array that contribute to the piezoelectric displacement of crystal dipoles, the amplitude of the vibration may be increased or decreased.

The frequency and amplitude of magnetic oscillators (74) and solenoids (76) may be controlled by managing the level and type of current to the devices and/or by mechanically altering the displaced mass. In the example of a solenoid (76), the amount of power supplied determines the acceleration of the core through the magnetic coil. Quick acceleration may produce more amplitude and slower acceleration may produce less amplitude. Also, increasing or decreasing the amount of weight attached to the core may correspondingly increase or decrease the amplitude of vibration. Techniques for controlling the frequency and amplitude of vibration generating devices are well known to those skilled in the art.

Figure 5:
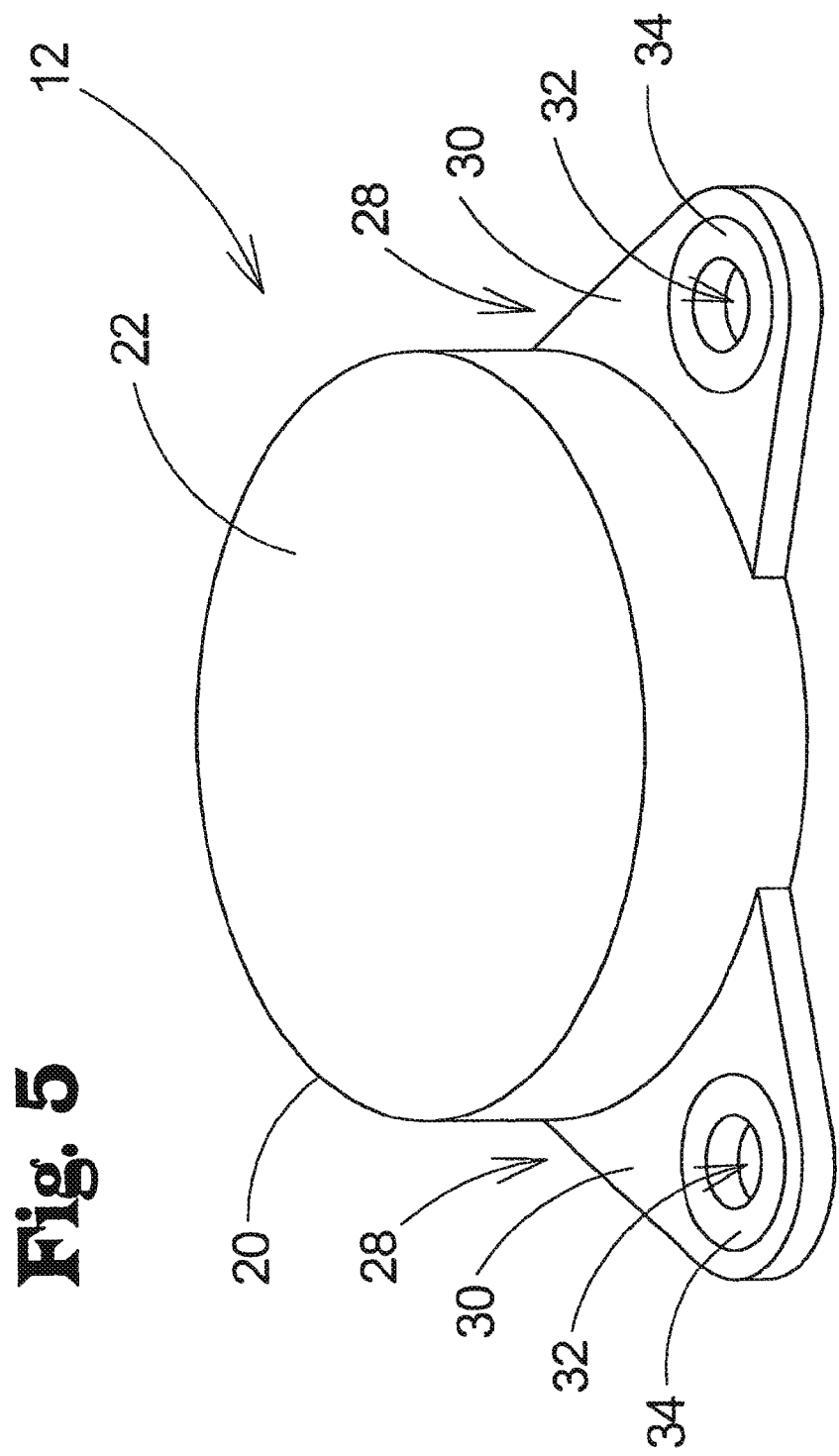
FIG. 5 is a schematic top perspective view of an implant device in accordance with an embodiment of the present invention.

FIG. 5 shows one embodiment of an implant device (12) of the invention. The exterior of the implant device (12) in this embodiment is generally disc shaped, which may facilitate or enhance the function of the implant device with respect to the tissue to be treated (through, for example, contact). The exterior shape may also optimize the function of the implant device (12) when used in certain locations within the patient (1). The shape of the case (20) of the device (12) is depicted as a simple disc, but the shape may include other contouring such as rounded edges and angles on the exterior surface may be sculpted to conform or correspond to the tissue that the implant device (12) may be in contact. The shape of the case (20) may vary widely and may be a function of the size and shape of the components housed in the interior (60), the manner in which the device (12) is to be secured in the patient, the contouring that provides the optimal effect on the targeted tissue, the location of the implant device (12) within the patient (1) conducive to desired effect, and the characteristics of the adjacent tissue.

The external elements of the implant device (12) include a case (20) that may be designed to form a hermetically sealed envelope that may provide a barrier between the internal elements within the interior (60) of the implant device (12) and the bodily tissue of the patient (1). The case (20) may be formed of a biocompatible material that would resist rejection by the body of the patient (1). Examples of such materials may include, for example, biocompatible metals, biocompatible polymers, silicone, glass, rubber, carbon, crystal, and the like. The selected material or materials should be of sufficient rigidity and durability to facilitate and preserve the function of the implant device (12). The case (20) may be formed of a combination of different materials to take advantage of structural and functional characteristics of the various materials.

To effectively locate the implant device (12) in the body of the patient (1), and also to resist dislocation or migration of the device within the body, it may be desirable to attach, mount or otherwise anchor the device (12) to bodily tissue. To facilitate the mounting of the implant device (12), the case (20) of the device (12) may include a primary mounting structure that forms a mount (28). The primary mounting structure or mount (28) as used herein is a feature or an extension of the exterior (22) of the case (20) that is generally integral to the case (20). The purpose of the mount (28) is to anchor the implant device (12) to tissue within the body of the patient (1) that is either near the target of the vibratory massage, can transmit the vibratory massage to the target or is the actual target of the vibratory massage. The mount (28) may include various structures depending on the specific manner of mounting. For example, the mount (28) structure may include a flange (30), an aperture (32), a clamp (56), a mesh (48), a groove (58), an engaging surface (24), a tine (26) and the like. A mount (28) can be attached directly to the bodily tissue of the patient (1), or the mount (28) may be employed with a secondary mounting structure, or mounting element (98), that mounts or attaches to the mount (28). A mounting element (98) as used herein is an element that is also employed to mount the implant device (12) in the body of the patient but is generally not integral to the case (20). Examples of mounting elements (98) that may be employed include an engaging surface (24), a tine (26), a screw (36), an aperture (32), a bolt (38) a nut (40), a plate (42), a line (44), a loop (46), a mesh (48), a suture (50), a staple (52) a band (54), a clamp (56), a groove (58), a chain, a pin, an adhesive, a hook, a rod, a wedge, a barb, an engaging thread, a brad, a nail, a rivet, a clip, a buckle, a hinge, a plug, a cap and the like. It is anticipated that when mounting an implant device (12) within a patient (1) that the implant device (12) may lack a mount (28) and rely on mounting elements (98) for its means of mounting. For example, an implant device (12) without a mount (28) may be placed on deep fascia (5) of a muscle and immobilized by overlaying a section of mesh (48) on top of the implant (12) and suturing the mesh (48) to the deep fascia (5). Similarly the implant device (12) without a mount (28) may be directly adhered to the deep fascia (5) or bone tissue (6) with biocompatible adhesives. Some locations for the implant device (12) may not require any means for mounting as the anatomical topography itself would deter or restrict movement or migration of the implant device (12) from the desired location. For example, if the implant device (12) is inserted into a bone, the bone tissue (6) itself may adequately secure the implant device (12) in the performance of its function. The specific type or types of mount, the combination of mounts (28), and/or the mounting elements (98) may be peculiar to the requirements of the location of the implant device (12) in the patient (1) and the desired effect for pain reduction or elimination.

A structure such as the tine (26) may comprise many forms and materials. For example, the tine (26) may include a metal barb, a polymer spine, a ceramic tooth, a crystalline spike and the like. A tine (26) may engage tissue to form a rigid attachment so that the vibratory waves produced by the implant device (12) may communicate through the attached tissue. The surface of the tine (26) may include an osteophillic treatment to promote bone tissue (6) growth on the surface of the tine (26) thus creating a stronger connection between the tine (26) and the bone. A tine (26) may be utilized as a mount (28) forming a part of the exterior (22) of the case (20) or may be utilized as a mounting element (98) either alone or in combination with other mounting elements, such as, for example on the jaws of a clamp (56) or forming a non skid surface of a band (54).

A flange (30) may encompass many shapes and may be composed of a variety of materials, such as metal, plastic, ceramic, carbon laminate, and the like. The mount (28) of an implant device (12) may include a flange (30) as part of the exterior (22) of the case (20). Similarly a flange (30) may be used alone, or form a constituent part of a structure including other mounting elements (98).

An aperture (32) is generally a hole formed in an object so that a second object can occupy the area of the hole. Often the relation between the two objects is to form a joint between or otherwise connect the two objects. An aperture (32) may be a part of a mount (28) used alone or in combination of other mounts (28) such as a flange (30), mesh (48), band (54), clamp (56) and the like. An aperture (32) may also be a mounting element (98) used alone or in conjunction with other mounting elements as a part of a mounting system.

A line (44) may take many forms, such as, for example, a metal wire, a fiber thread, a polymer filament, and/or a combination of braided/twisted or layered materials forming a tendon. Depending on the resilience of the materials employed, a line (44) may also provide a buffering function between the implant device (12) and the tissue to which the line (44) is connected. The degree of rigidity, flexibility and elasticity of the line (44) may determine if the line (44) is able to communicate or absorb mechanical vibratory waves between the supporting tissue and the mounting elements (98).

A loop (46) may form a closed or partly open curve within itself through which another material may extend or be encompassed. The loop (46) may comprise any material suitable to engage bodily tissue and/or other mounting elements (98). As a mount (28), the loop (46) may comprise the entirety of the implant device (12) and have the form of, for example, a ring, a crescent or a hemispheric-shaped element to encompass or surround in whole or in part some portion of body tissue. In other forms, a limited portion of the exterior (22) of the case (20) of the implant device may form a closed or partly open curve. The loop (46) may also be a mounting element (98) that is utilized singularly or in conjunction with other mounting elements (98) such as a flange (30), screw (36), bolt (38), nut (40), plate (42), line (44), mesh (46), band (54), clamp (56) and the like.

Mesh (48) may have many forms and comprise various materials. For example, the mesh (48) may comprise a sheet of metal material with a plurality of holes formed therein, or may also comprise a textile structure of threads or a network of filaments. The mesh (48) may form a mount (28) on the exterior (22) of the case (20) of an implant device (12). The mesh may also form a mounting element (98) that is utilized as a means for mounting the device (12) to tissue either alone or in combination with other mounting elements.

A band (54) is generally a strip of material used to bind one object to another object or to confine, restrict or restrain an object with respect to the other object. A band (54) may be constructed of a wide variety of materials and may form either an open or closed circle. A band may include means to secure one end of the band to an opposite end of the band (such as, for example, a belt buckle on a belt, hook and loop fasteners on a bra, a master link on a bicycle chain, and the like). A band (54) may be a mount (28) or a mounting element (98) as defined herein in a means for mounting an implant device (12) within the body of a patient (1).

A clamp (56) may include a pair of gripping surfaces that are biased towards one another in opposition to secure an object or objects positioned in between the surfaces. A clamp (56) may be formed by the entirety of the implant device (12), possibly having sections of the device (12) each having one of the gripping surfaces, and the interior (60) may be divided among the sections with the components of the implant device (12) located in each of the sections. Optionally, a limited portion of the case (20) may form either one or both gripping surfaces and function as a mount (28). As a mount, the clamp may be used alone or with other mounting elements (98). The clamp (56) may also be utilized as a mounting element (98) either singly or in combination with other mounting elements (98) in a means for mounting an implant device (12) within the body of a patient (1).

A groove (58) may be a channel or depression formed in the exterior (22) of the case (20) of an implant device (12) so that other mounting elements (98) may engage the groove (58) to mount the implant device (12), but it should be recognized that the invention is not so limited. A groove (58) in the exterior (22) of the case (20) may be utilized to engage bodily tissue such as an artery, a vein, a tendon, a ligament, a bone, and that like as a means for mounting the implant device, either alone or in conjunction with other mounting elements (98), in the body of the patient (1).

A buffer (34) may function either as a mount (28) or a mounting element (98) that has the ability to provide a degree of dampening of the vibratory wave action produced by the implant device (12) before the wave action reaches the tissue to which the buffer is connected. For example, a line (44) may function as a buffer (34) element if the material forming the line exhibits elastic, resilient and/or flexible characteristics that attenuate or prevent the communication of a portion of the vibratory wave action along its length. As another example, a mesh (48) may function as a buffer (34) element if the structural composition or its constituent material of the mesh (48) generally inhibits the communication of the vibratory waves emanating from the implant device (12) through the mesh. As yet another example, as illustrated in FIG. 5, each of the apertures (32) positioned in the flanges (30) includes a ring of flexible material that functions to dampen the vibration produced by the implant device (12) from being transmitted to a mounting element (98) engaging the aperture (32).

One embodiment of a mount (28) on the exterior (22) of the case (20) is illustrated in FIG. 5. The mount (28) takes the form of a flange (30) that includes an aperture (32).

Figure 6:
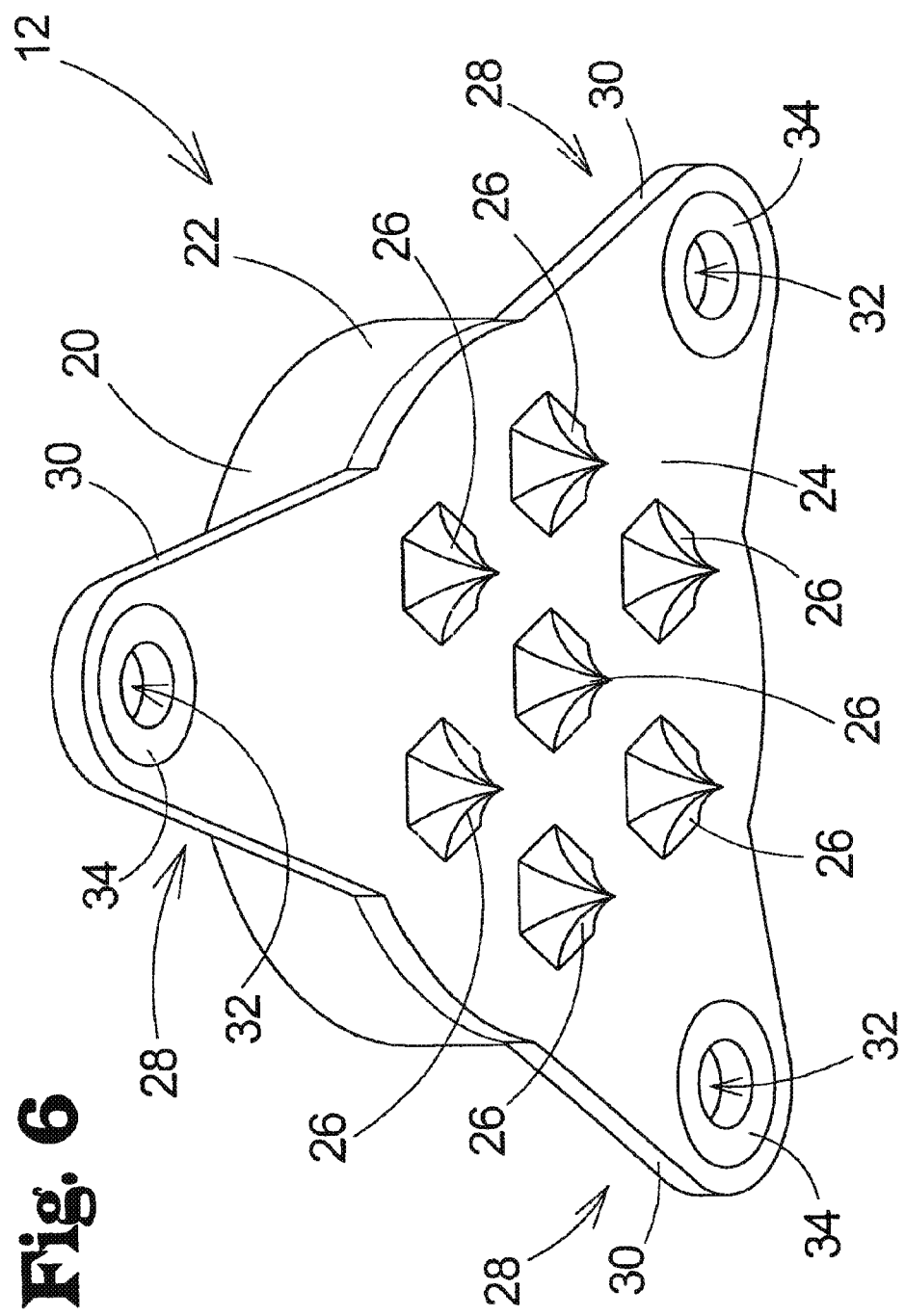
FIG. 6 is a schematic bottom perspective view of the implant device of FIG. 5 in accordance with an embodiment of the present invention.

In FIG. 6, the embodiment of the implant device (12) includes an engaging surface (24). A section of the exterior (22) of the case (20) may be designed to engage a specific type of tissue within the body of the patient (1) so that the implant device (12) may be held in an optimal position to administer the vibratory massage. In FIG. 6 the engaging surface (24) comprises a relatively flat surface with tines (26) designed to engage tissue (6) such as, for example, bone. This particular structure may be suitable for mounting the implant device (12) on a relatively flat section of bone tissue (6) such as, for example, the scapula, and the ileum of the pelvis, the sternum, a rib, the mandible or the other bones of the skull. Functionally, the embodiment illustrated in FIG. 6 may have the engaging surface (24) pressed against bone tissue (6) so that the tines (26) penetrate into the bone tissue (6) to provide a suitable connection to transmit vibratory waves to not only the bone but also the bodily tissue that contacts the bone. The mount (28) takes the form of a flange (30) and an aperture (32) and may be anchored to the bone through the use of screws (36) that pass through the aperture (32) and may be screwed into the bone tissue (6). To prevent direct communication of vibration between the case (20) and the anchoring screws (36), a vibration isolating buffer (34) may be placed between the aperture (32) and the screws (36). The use of the buffer (34) may prevent the vibration of the implant device (12) from vibrating the screws (36) loose from the bone tissue (6). It is anticipated that the tines (26) may include additional features to better fix the implant device (12) to the bone tissue (6). For example, the tines (26) may include an ectopic porous coat possibly used in conjunction with a morphogenic protein, or a hydroxyl apatite coating to form an osteophillic surface so that bone tissue (6) would more thoroughly engage with the engaging surface (24) on the exterior (22) of the case (20).

Figure 7:
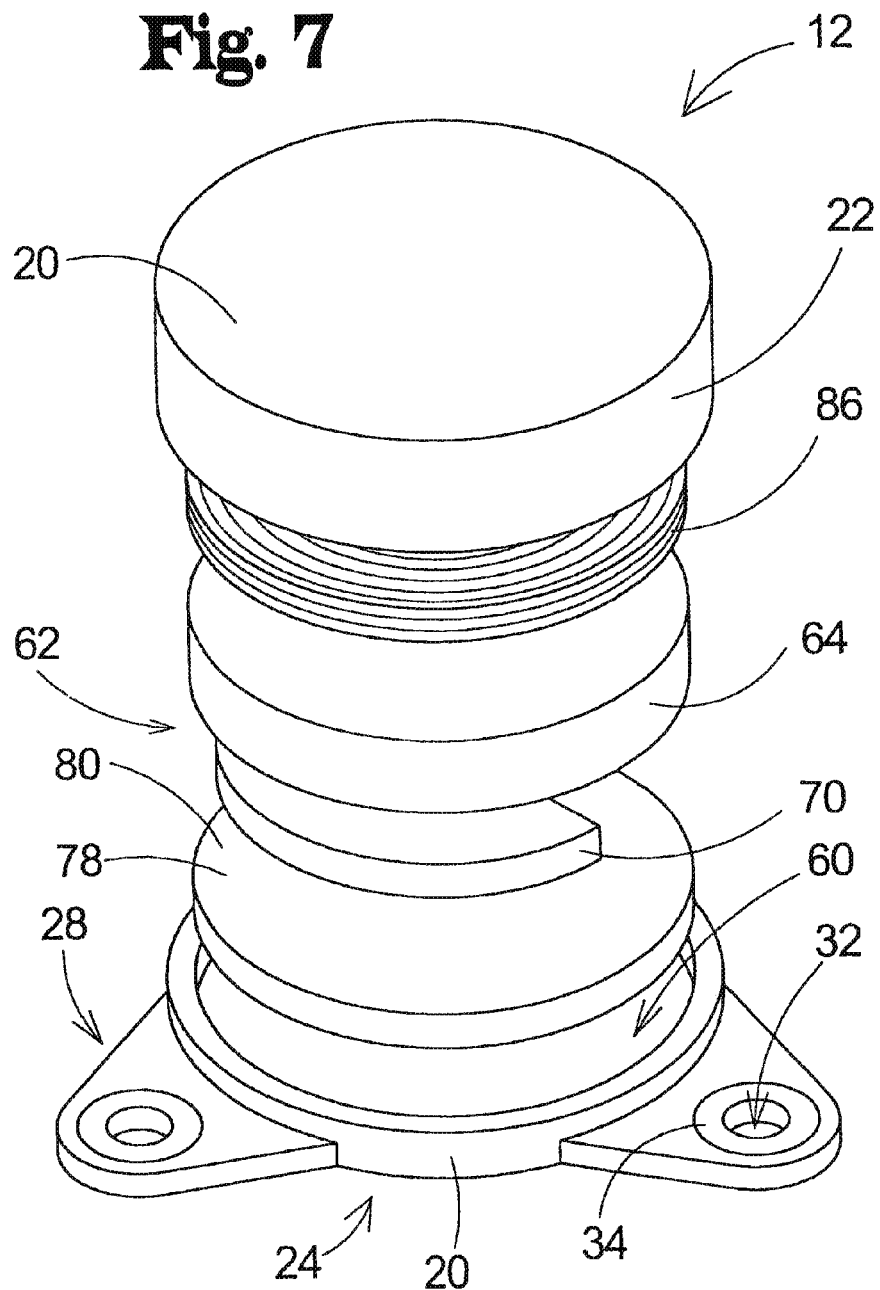
FIG. 7 is a schematic exploded view of the implant device of FIG. 5 in accordance with an embodiment of the present invention.

FIG. 7 illustrates constituent elements located in the interior (60) of the implant device (12) of the embodiment exhibited in FIGS. 5 and 6. The exploded view reveals that the individual elements may be layered within the disc shaped case (20). One layer within the disc shaped case (20) may be the receiving coil (86) which may be comprised of a spiral of fine wire designed to receive power in the form of electromagnetic induction from a transmitting coil (88). Positioned in the center of the receiving coil (86) may be the receiver (92) and the switch (90). Another layer may include the vibration generator (62), which may comprise a motor (64) and a flywheel (70) having an eccentric mass. The motor (64) in this embodiment is a disc motor (68) with the large mass portion of the eccentric flywheel (70) occupying a radius substantially coextensive with the disc motor (68). Another layer may include the power supply (78) such as a battery (80), and illustratively a button cell battery (80). It will be appreciated that the positioning or order of the various layers may be different within the implant device (12) depending on various factors such as the specific effect desired, optimization of the components, and manufacturing considerations.

Figure 8:
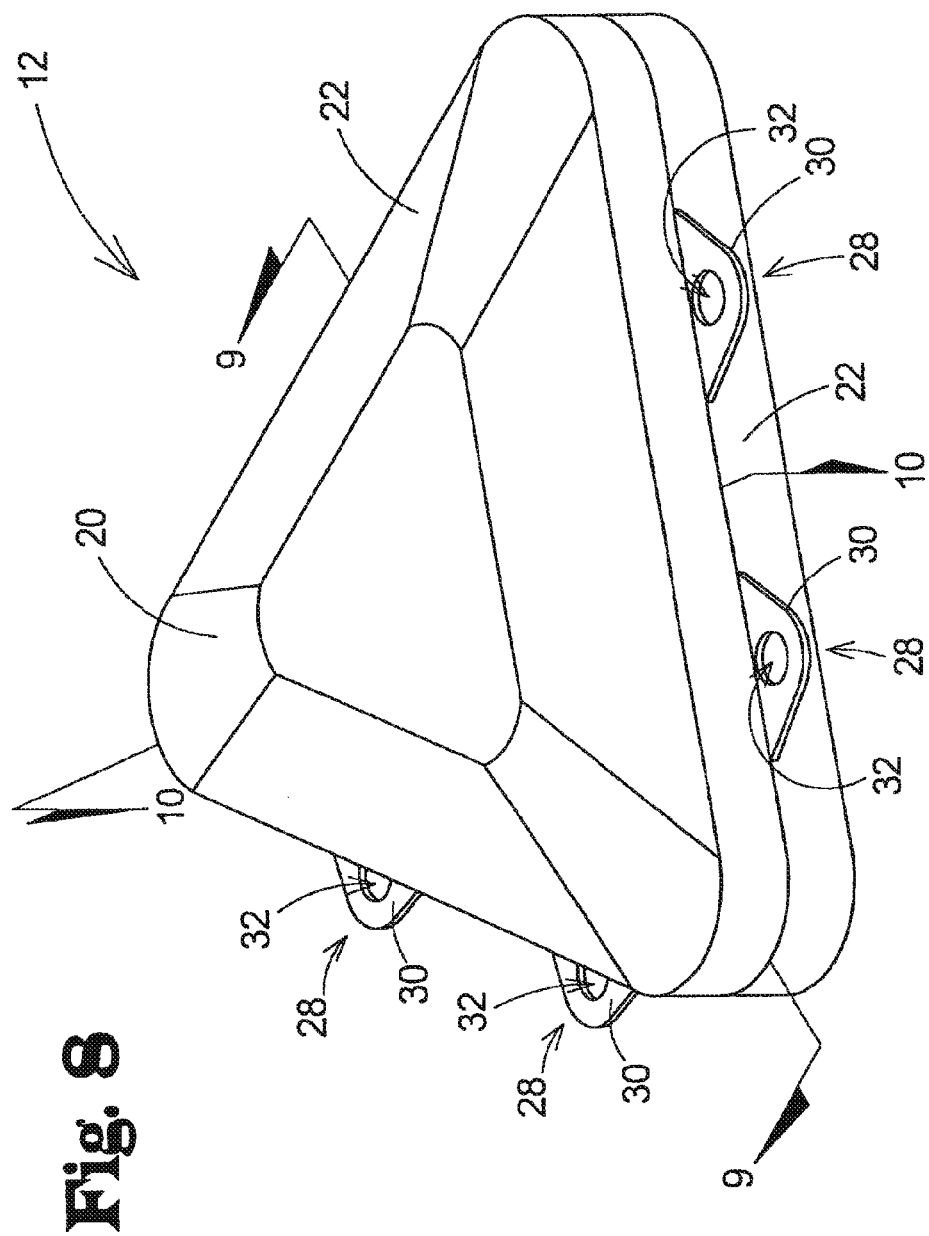
FIG. 8 is a schematic perspective view of another implant device in accordance with an embodiment of the present invention.
Figure 9:
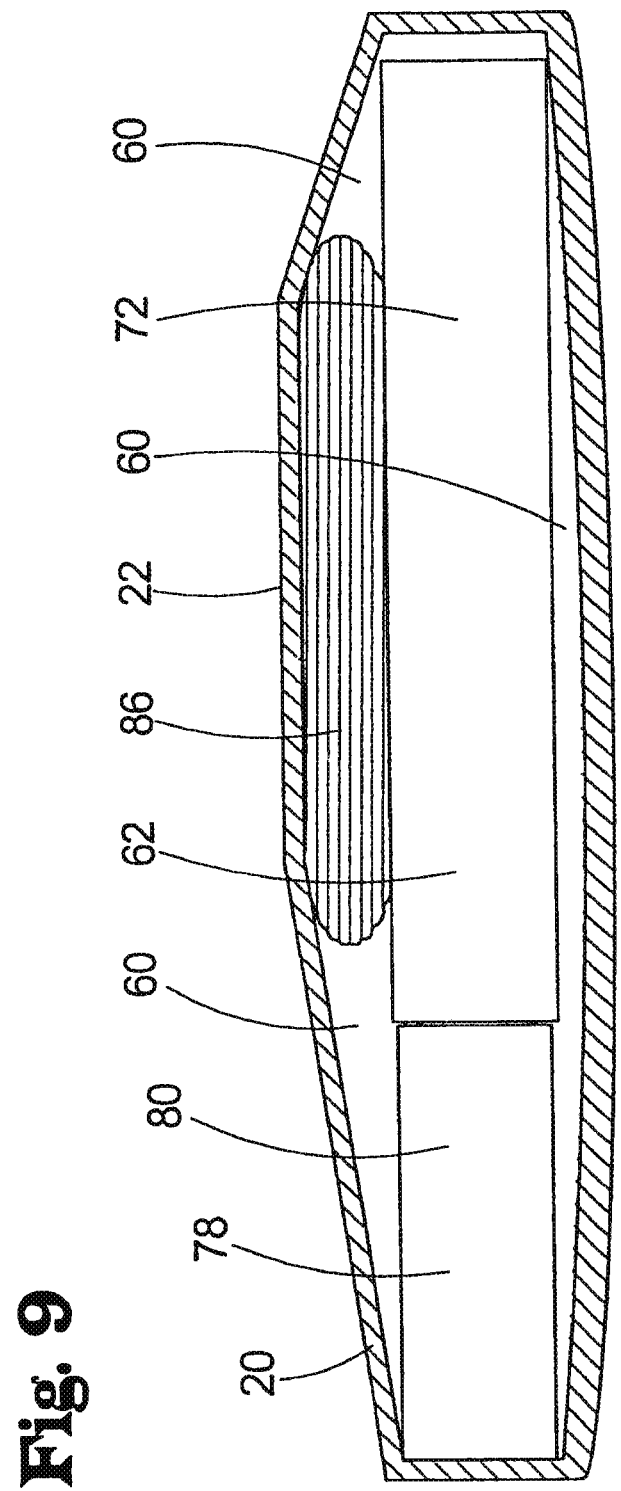
Figure 10:
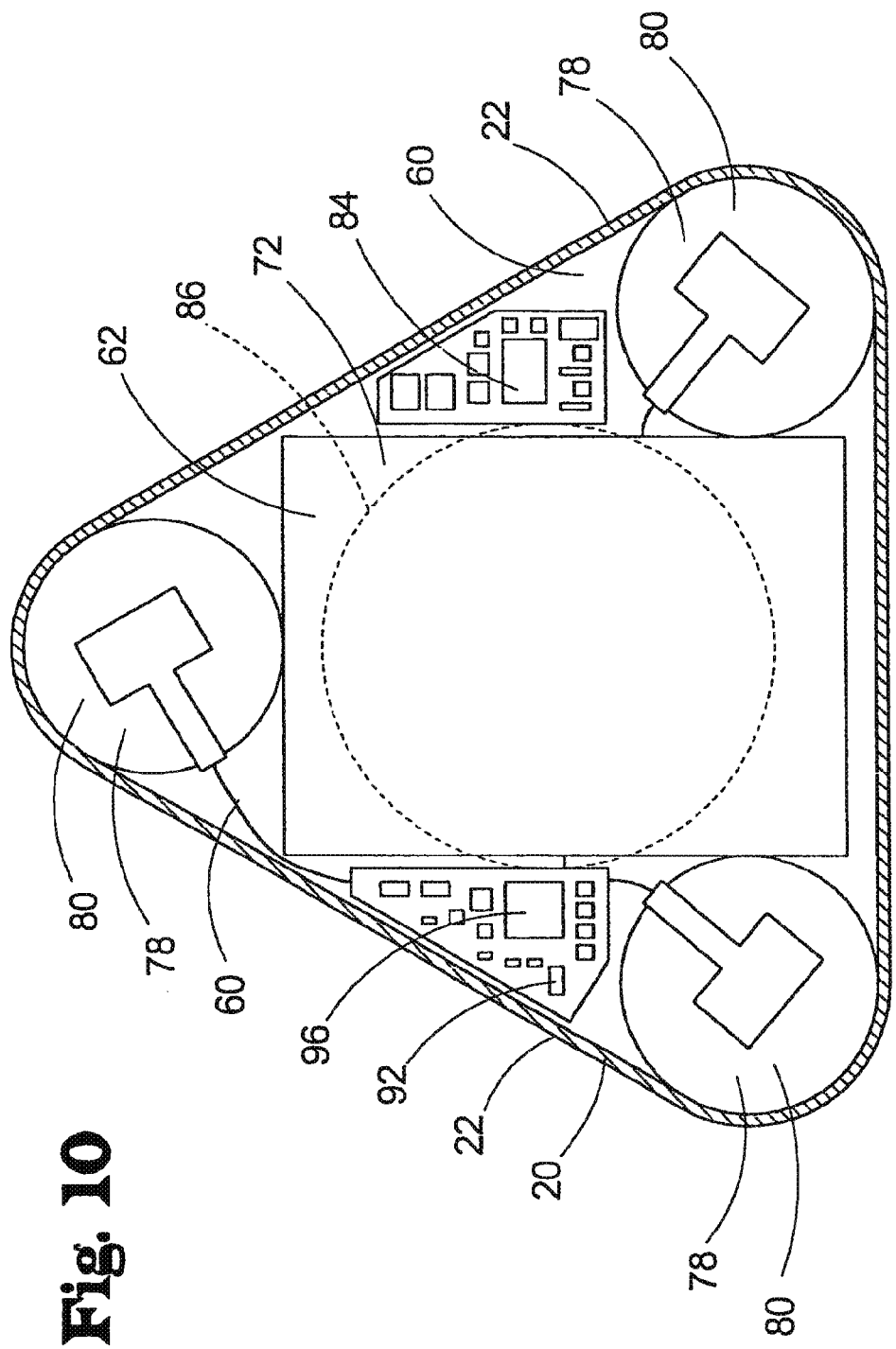
FIG. 10 is a schematic top cross sectional view of the implant device of FIG. 8 in accordance with an embodiment of the present invention.

Another embodiment of the implant device (12), illustrated in FIG. 8, may be generally flat but not disc shaped. Like the embodiment previously described, the exterior (22) of the case (20) may include mounts (28) in the form of flanges (30) with apertures (32). The cross section of this embodiment illustrated in FIG. 9 shows that the interior (60) components are not layered as in the previous embodiment but may be positioned within the interior (60) based on the space available and the shape of the component. The vibration generator (62) in this embodiment is a piezoelectric vibrator (72) which is in the form of a block that may contain a single or a series of stacked transducers to produce vibration. The receiving coil (86) may be located between the vibration generator (62) and the case (20) to take advantage of the largest open circular area. FIG. 10 illustrates the placement of three button cell batteries (80) which comprise the power supply (78). The elements of the receiver (92), the charging circuit (84) and the micro processor (96) may be integrated into printed circuit boards that occupy the remaining interior (60) space.

Figure 11:
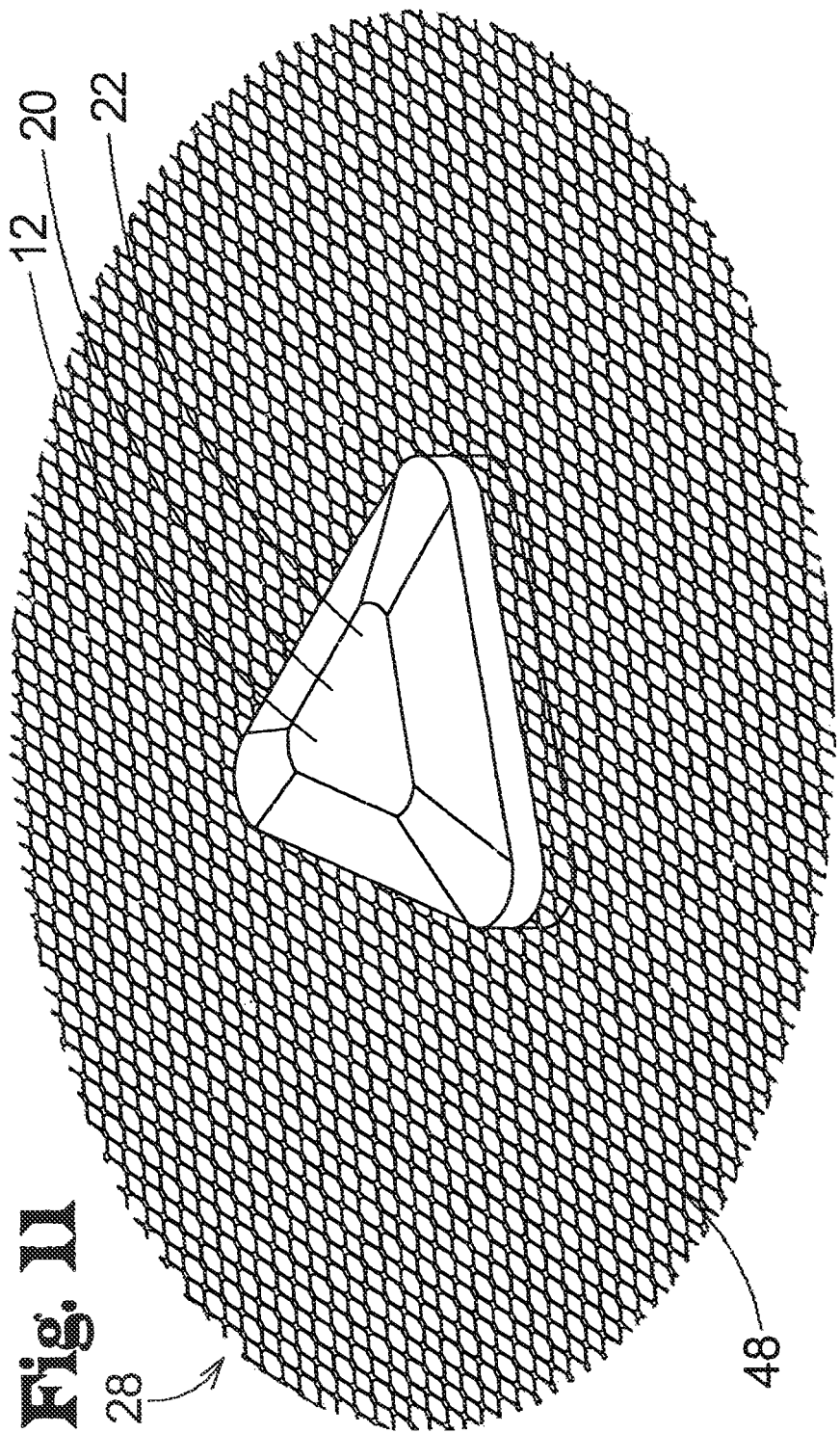
FIG. 11 is a schematic perspective view of the implant device of FIG. 8 utilizing a mesh mounting method.

FIG. 11 depicts the embodiment of the implant device (12) of FIGS. 8 though 10 with a mount (28) in the form of a mesh (48). The mesh (48) in FIG. 11 is attached to the exterior (22) of the case (20) of the implant device (12) along an equatorial plane, which may have a seam or joint between complimentary sections of the case (20), but the invention is not so limited. It is anticipated that a mount (28) in any form could be connected to the exterior (22) of the case (20) at any point or even formed as part of the case (20).

The embodiment illustrated in FIGS. 8 through 11 may be configured for mounting the implant device (12), for example, on or near an organ or within relatively soft muscle tissue (4) or upon the deep fascia (5) of striated muscle tissue (4). It is anticipated that the entire exterior (22) surface area of the case (20) of the implant device (12) may constitute an engaging surface (24). In this embodiment, the tissue that the engaging surface (24) may engage with may be organ tissue, muscle tissue (4) or deep fascia (5).

Figure 12:
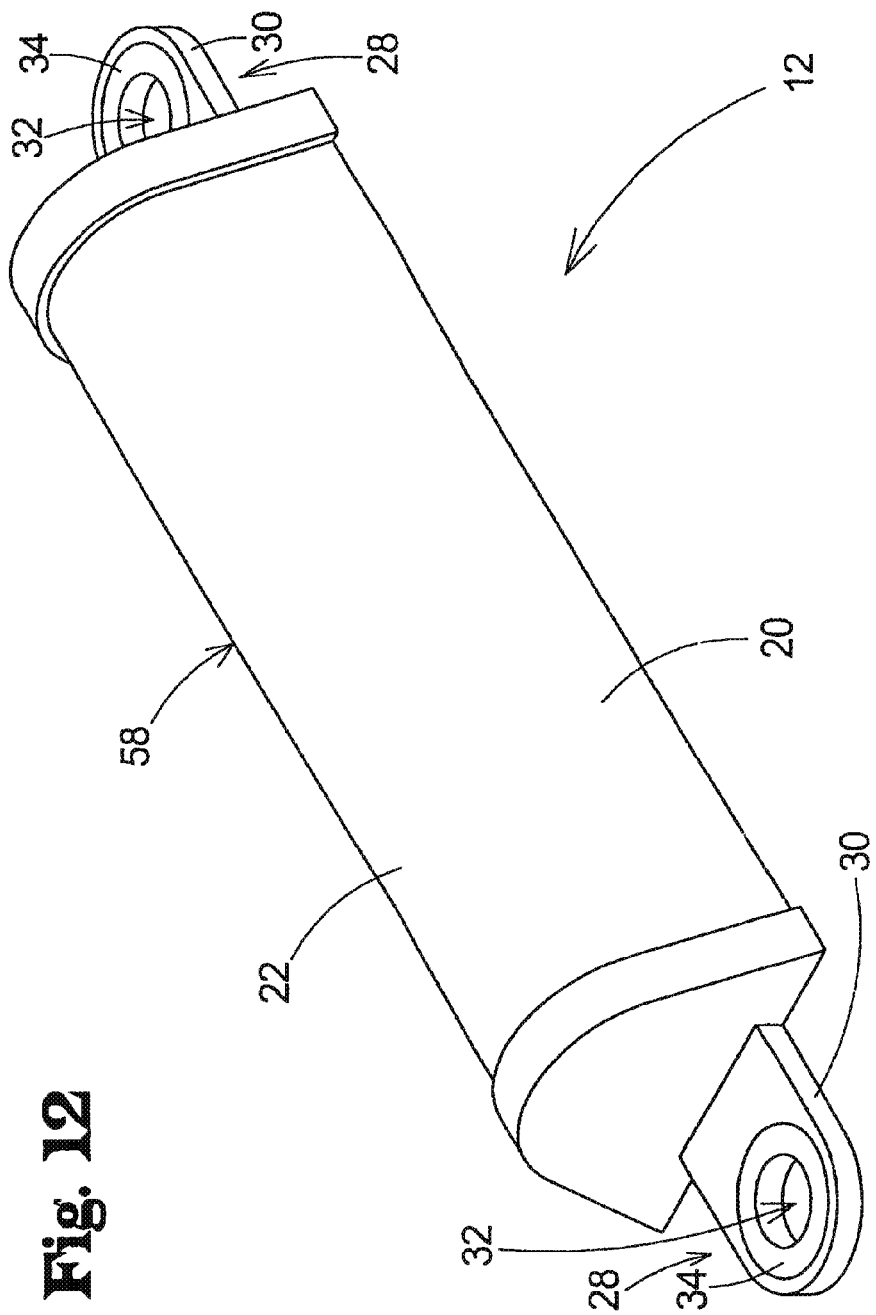
FIG. 12 is a schematic top perspective view of yet another implant device according to an embodiment of the present invention.

A third embodiment of the implant device (12) is illustrated in FIG. 12. In this embodiment the implant device (12) demonstrates some of the same characteristics as the embodiment illustrated in FIG. 5 but the structure of the implant device (12) takes a different shape. Similar to the disc shaped embodiment of FIG. 5, the embodiment of FIG. 12 includes mounts (28) in the form of flanges (30) with apertures (32) for accepting an appropriate mounting element (98) such as, for example, a screw (36), bolt (38), nail, brad, line (44), suture (50), staple (52), detent, ring and the like. The exterior (22) of the case (20) also includes a groove (58) that is in the form of a depressed region located between ridges located at the proximal and distal ends of the implant device (12). The depressed region of the groove (58) may facilitate the use of a band (54) or other mounting elements (98) such as, for example, a staple (52), suture (50), mesh (48), clamp (56) or a line (44) that may extend into and engage the groove (58) and connect with other nearby tissue.

Figure 13:
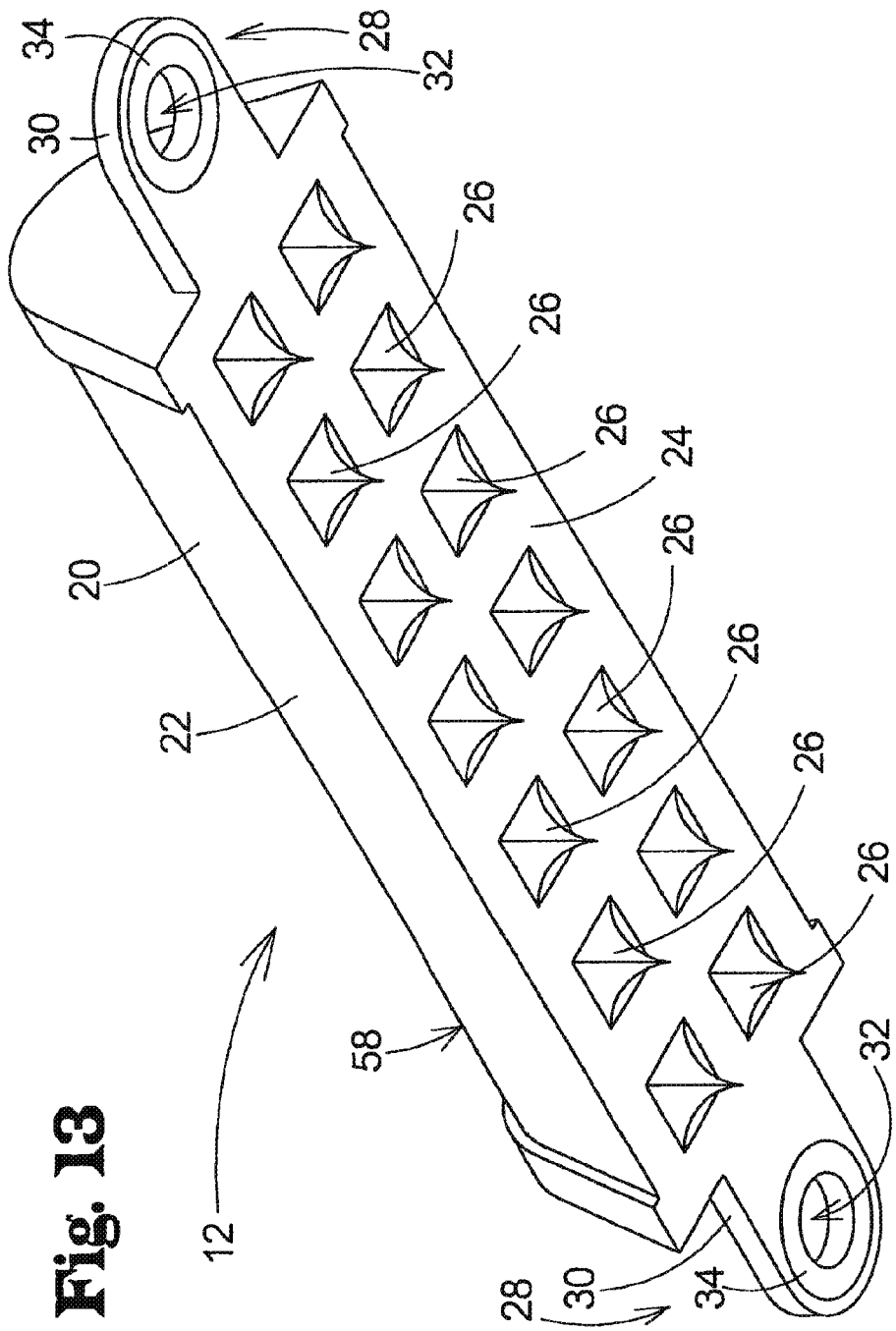
FIG. 13 is a schematic bottom perspective view of the implant device of FIG. 12 according to an embodiment of the present invention.

FIG. 13 shows the engaging surface (24) of the embodiment of the implant device (12) depicted in FIG. 12. Similar to the embodiment depicted in FIG. 6, the engaging surface (24) is generally flat and includes bone engaging tines (26) that may or may not be used in conjunction with the mounts (28).

Figure 14:
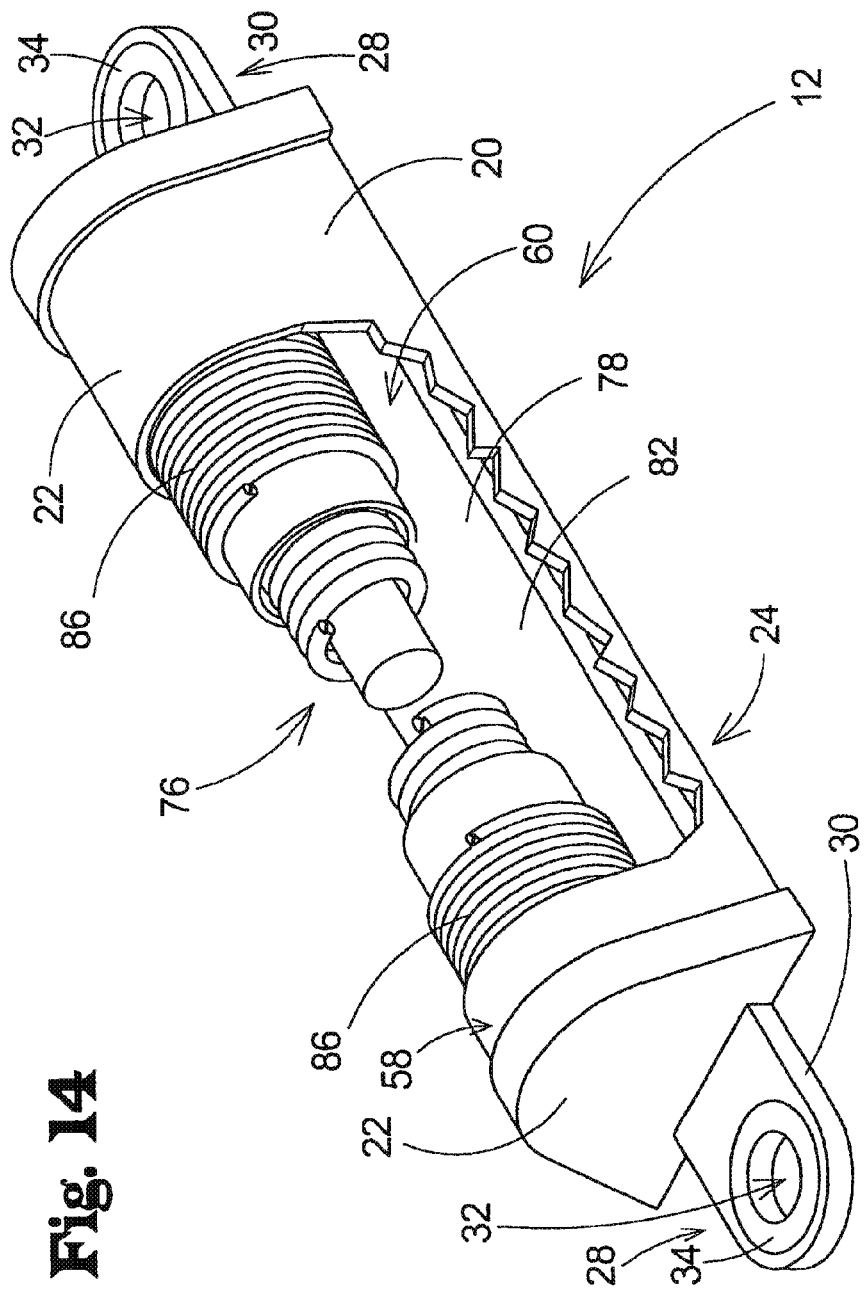
FIG. 14 is a schematic exploded view of the implant device of FIG. 12 in accordance to an embodiment of the present invention.

FIG. 14 is an exploded view of the embodiment shown in FIGS. 12 and 13 that illustrates elements located in the interior (60) of the implant device (12). In this and other embodiments, the receiving coil (86) forms an outer tube, in which some of the other interior (60) elements reside. The vibration generator (62) in this embodiment is in the form of a solenoid (76) which may be moved by magnetic forces along a substantially cylindrical access way formed by two electromagnetic coils which generate the magnetic forces that cause the solenoid (76) to produce vibrations. The self-contained power supply (78) in this embodiment is in the form of a battery (80) that conforms to the interior (60) shape of the exterior (22) engaging surface (24). To take advantage of all of the available space the battery (80) in this embodiment is a flat battery (82).

Figure 15:
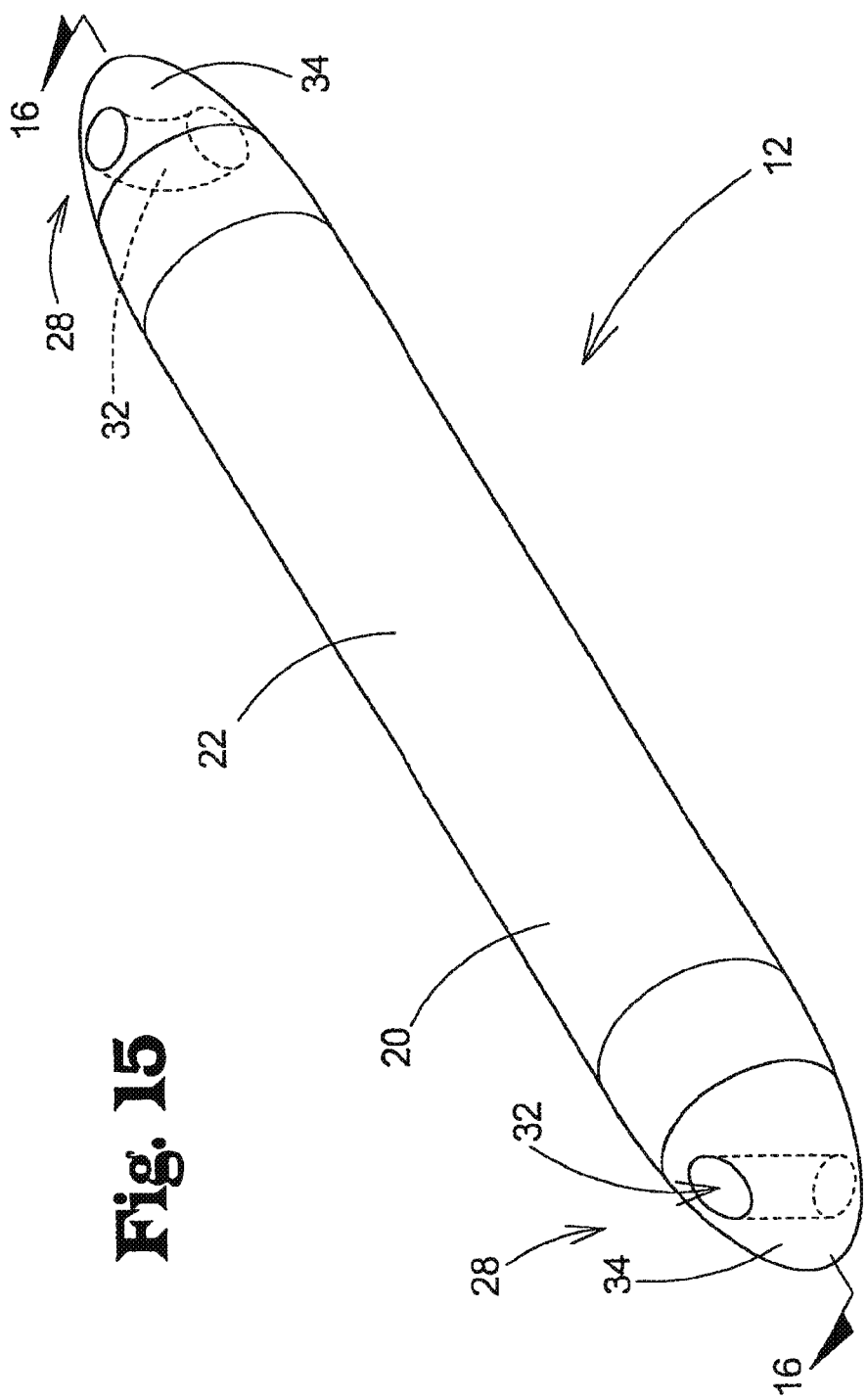
FIG. 15 is a schematic top perspective view of a different embodiment of an implant device according to an embodiment of the present invention.

FIG. 15 shows another embodiment of an implant device (12) which has an exterior that is substantially cylindrical in shape. At each end of the case (20) may be mounts (28) that may have a substantially conical shape. An aperture (32) may be included in each mount (28). In FIG. 15, the proximal aperture (32) extends through the mount (28) in a substantially straight and linear fashion while at the proximal end the aperture (32) extends through the mount (28) in a non-linear and generally curved manner. The characteristics of the aperture (32) in any embodiment of the implant (12) may reflect the specific method of mounting that is desired for or required by the particular placement of the implant device (12) within the patient (1). The mount (28) that is illustrated in FIG. 15 may comprise a material that would function as a buffer for the vibrations produced by the implant device (12).

Figure 16:
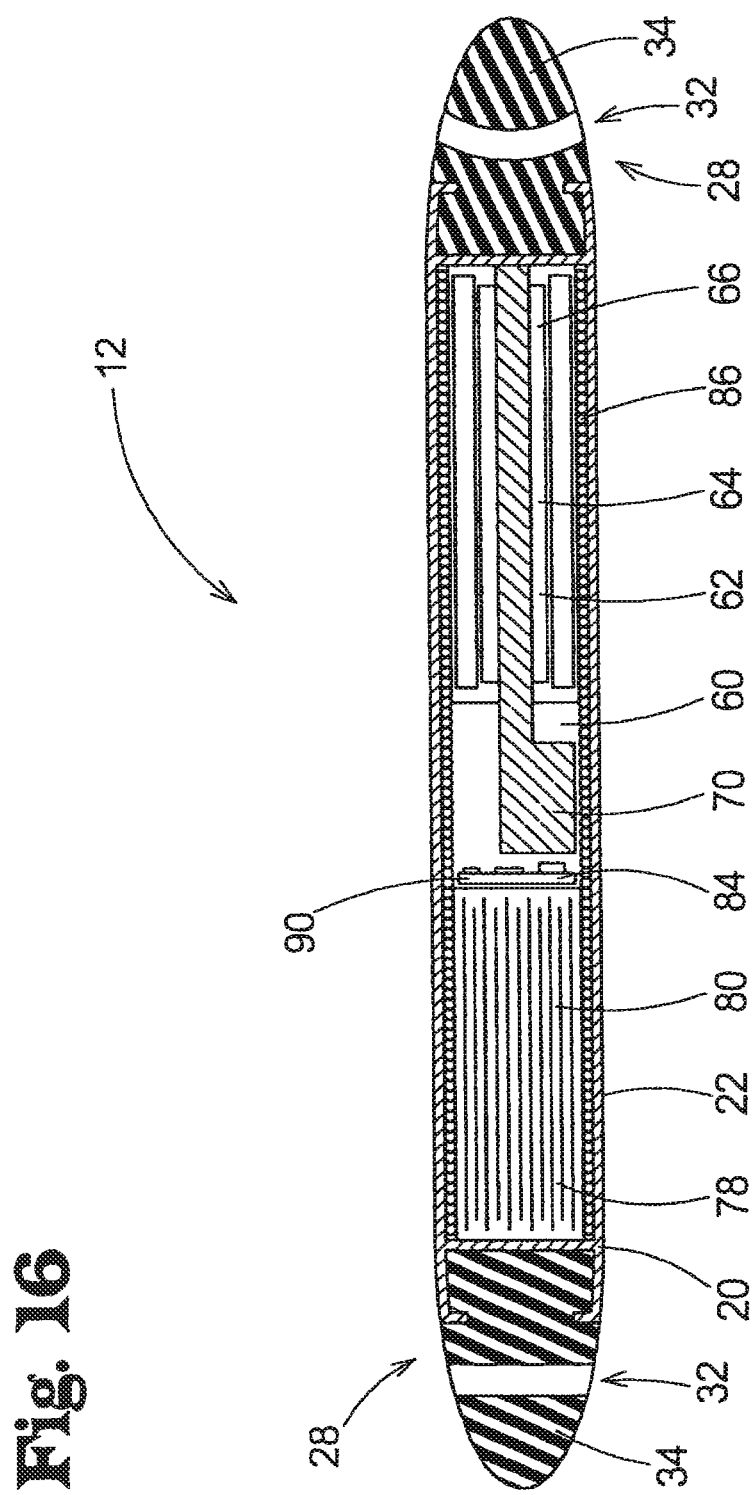
FIG. 16 is a schematic cross sectional view of the implant device of FIG. 15 according to an embodiment of the present invention.

As illustrated in FIG. 16, the distribution of elements in the interior (60) may be dictated by the shape of the exterior (22) of the case (20). In the embodiment depicted in FIGS. 15 through 17 the receiving coil (86) is configured with a tube like structure inside the interior (60) of the case (20). Positioned inside the receiving coil (86) may be the vibration generator (62), which is illustratively a motor (64), and may be a cylindrical motor (66). The shaft or axle of the motor (64) may be attached to a flywheel (70) which has an eccentric mass. At the opposite end of the interior (60) of the case (20) is the internal power supply (78) which is depicted in this embodiment as a battery (80) that may have a cylindrical shape. Between the power supply (78) and the vibration generator (62) may be a printed circuit board which may contain a switch (90), a charging circuit (84), a receiver (92) and/or a microprocessor (96).

FIG. 18 illustrates another embodiment of the implant device (12) in which the exterior (22) of the case (20) has a generally an ovoid shape. The mount (28) shown in FIG. 18 comprises a groove (58) that may be engaged by a band (54) functioning as a mounting element (98) that may attach the implant device (12) to other mounting elements (98), such as, for example, a pair of clamps (56), a number of apertures (32) and a line (44) forming a loop (46). In this embodiment of the implant device (12), means for mounting are employed for the purpose of mounting the implant device (12) between the spinous process (9) of two adjoining vertebrae (8). For this positioning of the implant device (12), the mounting structure includes a pair of connected clamps (56) which are spring biased and are shown clasping each of the spinous processes (9). Both clamps (56) include a group of tines (26) that engage and penetrate the bone tissue (6) of their respective spinous process (9). One of the clamps (56) utilizes the set of apertures (32) on the distal ends of the clamp (56) which are interthreaded with a line (44) between the opposing jaws of the clamp (56). The line (44) completes a loop (46) with the jaws of the clamp (56) encircling the spinous process (9) of one of the vertebrae (8). It is anticipated other combinations of mounts (28) and/or mounting elements (98) may also be utilized in this area, to achieve similar effects. The actual implant device (12) may be attached to the clamp (56) by the band (54). The band (54) may be a part of, or connected to, the clamp (56) which engages the groove (58) of the exterior (22) of the case (20) of the implant device (12). The band (54) in this embodiment includes a mechanism for tightening the band (54) to form a stable connection to the mounting means.

Figure 19:
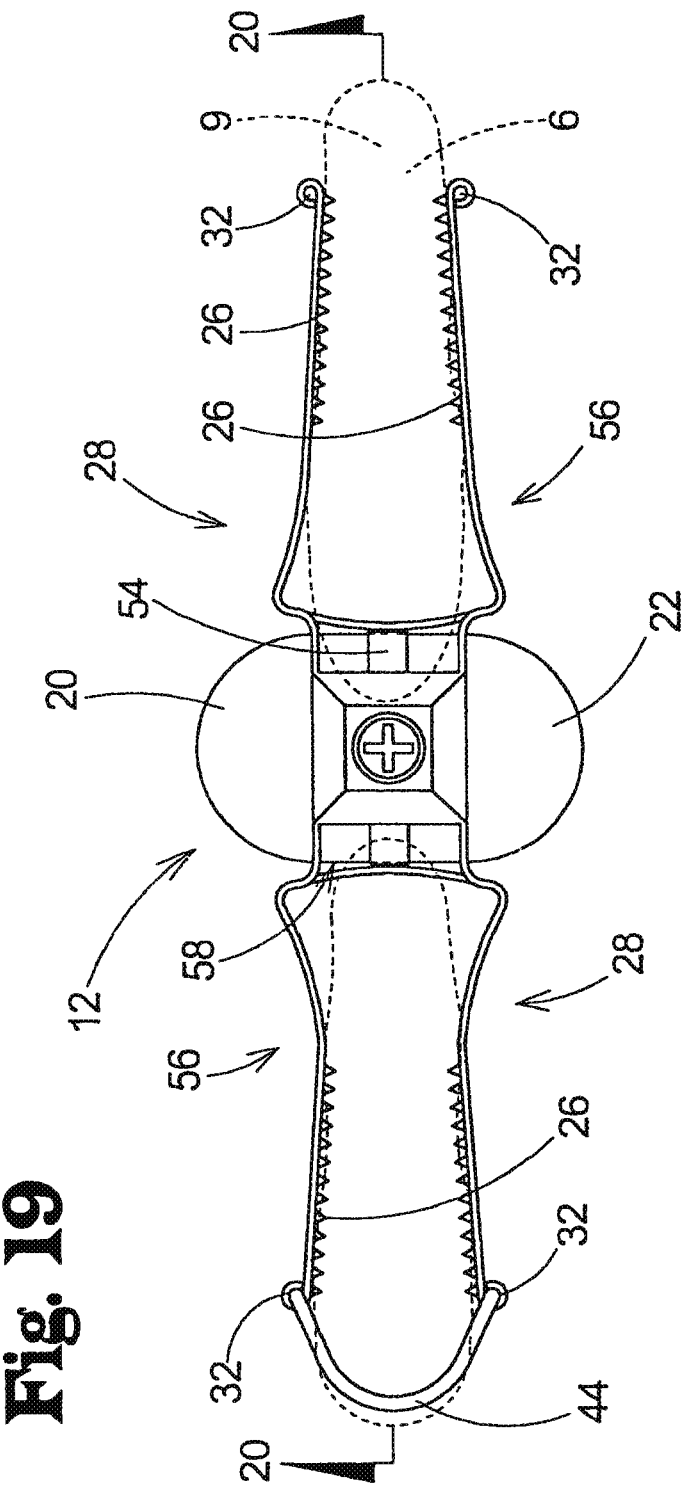
FIG. 19 is a schematic top view of the implant device of FIG. 18 with accompanying mounting elements in accordance with an embodiment of the present invention.
Figure 20:
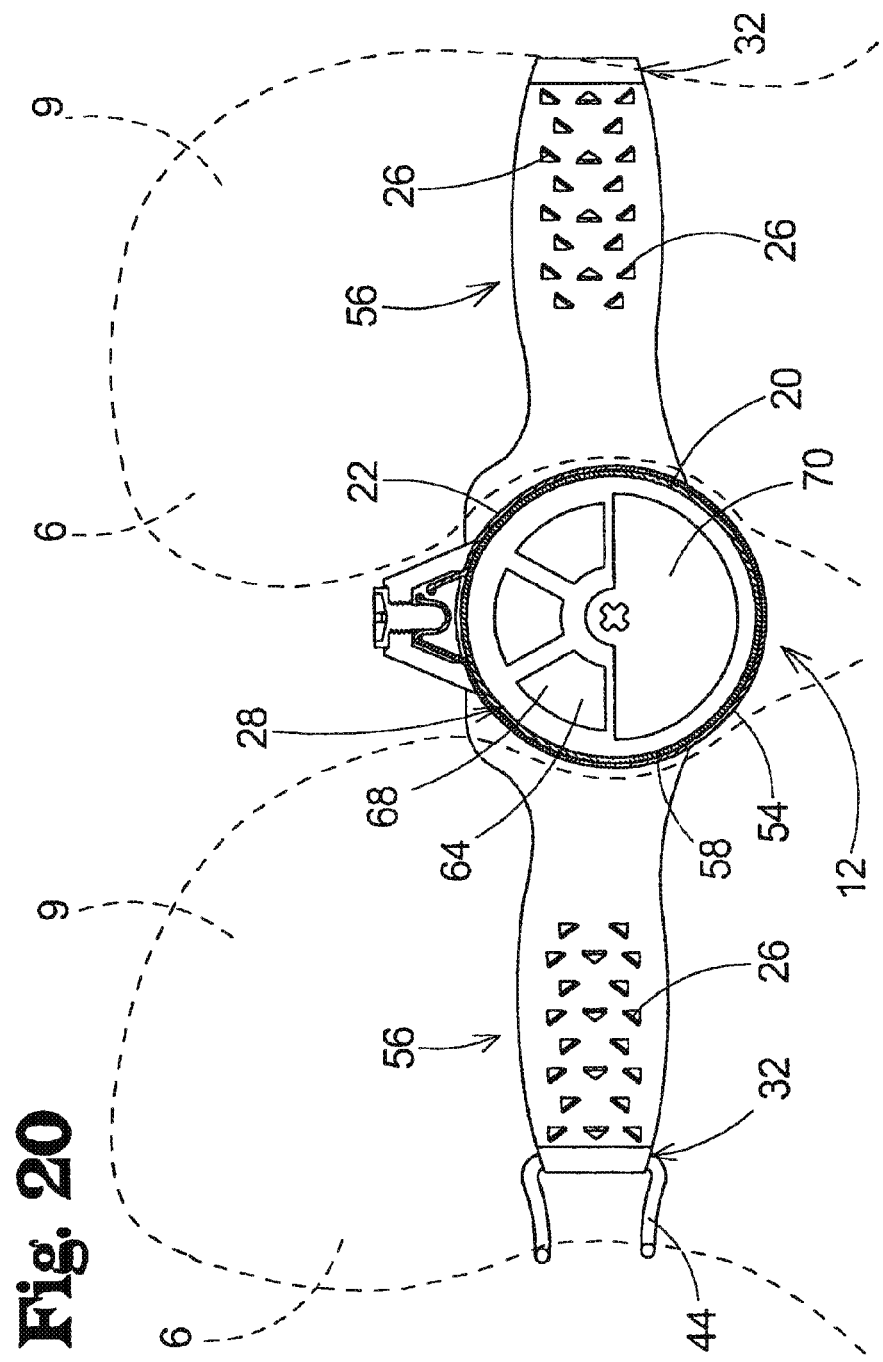
FIG. 20 is a schematic side cross sectional view of the implant device of FIG. 18 according to an embodiment of the present invention.

The embodiment depicted in FIGS. 19 and 20 includes structures suitable for treating some more specific locations and conditions of a patient (1). For example, a patient (1) may suffer spinal trauma which produces pain. The implant device (12) may be placed as close to the affected area of the body of the patient as possible to optimize the effect of the vibratory massage. In areas targeted for administration of vibratory massage that are densely packed with muscle, ligament, tendon (7) and bone it has been determined that transmitting or distributing the vibratory massage through the targeted area of the vertebrae (8) has significant benefit. A relatively rigid structure for attaching the implant device (12) to the vertebrae (8) is suitable for attaining such a benefit. An ovoid shape for the exterior (22) of the case (12) may be suitable for fitting the space between the adjacent spinous process (9). The capability of the vertebrae (8) to function as a vibratory communication medium is enhanced by the use of a structure providing a rigid mounting between the implant (12) and the vertebra, and a suitable mounting structure may employ a clamp (56). A double clamp (56) mounting may have the added function or benefit of immobilizing the targeted vertebrae (8) to prevent further damage. The design of the mounting structure employed may also take into consideration the eventuality that the implant device (12) may later be removed from or replaced in the patient (1) while leaving the implanted mounting structure within the patient (1).

The symptoms of the patient (1), the location of the implant device (12) in the patient, and/or prognoses of the patient may call for significantly different combinations and configurations of the implant device (12), including the shape of the exterior (22) of the case (20), the elements in the interior (60) of the implant device, the number of the implant devices (12) employed, and the type, number and configuration of the mounting elements (98) employed. The areas of the body to be administered to, the range of anatomical topographies, and the plurality of desired effects, all contribute to the wide variety of component forms and arrangements for the implant device (12) that may be utilized.

Figure 21:
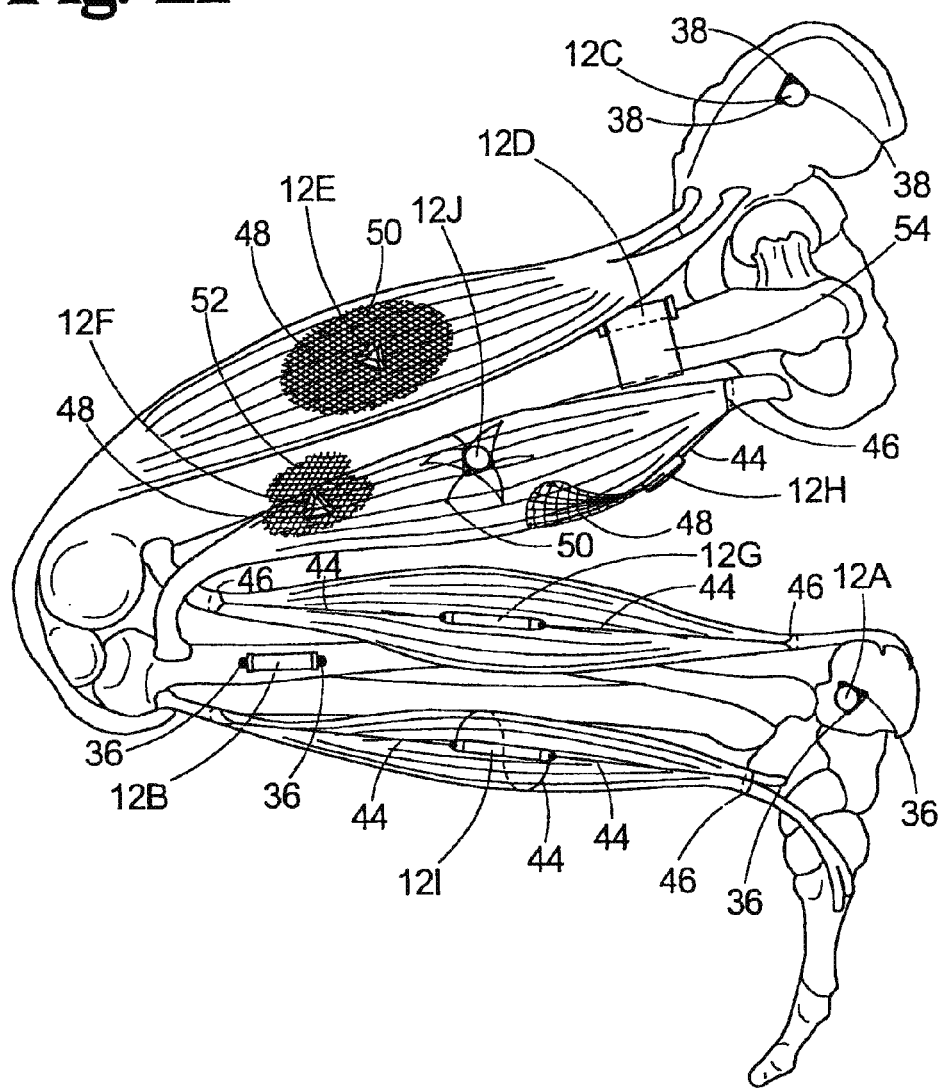
FIG. 21 is a schematic anatomically exploded view of a leg illustrating various methods of mounting various implant devices in accordance with various embodiments of the present invention.

FIG. 21 illustrates a number of various configurations for the implant devices (12) utilizing different mounting structures according to the present invention.

Implant device (12A) in FIG. 21 depicts an implant device similar to the embodiment depicted in FIGS. 5 through 7, which is illustratively shown attached to the bone tissue (6) of the calcaneus or heel bone. The case (20) of the implant device (12) includes an engaging surface (24) which is contoured to substantially conform to the topography of the area of the calcaneus bone to which the implant device (12) is attached. The engaging surface (24) includes a number of tines (26) to anchor the implant device (12) solidly to the bone tissue (6) and to transmit the vibrations generated by the implant device (12) to tissue in contact with the bone. The implant device (12) may be additionally secured to the heel bone by a number of screws (36) which pass through an aperture (32) located in a flange (30) of a mount (28) on the implant device. A buffer (34) may be included between the aperture (32) in the flange of the case (20) and the screws (36) to attenuate or isolate the screws (36) from vibrations of the case (20) that may loosen the screws (36) or damage the bone tissue (6) if transmitted without some degree of attenuation to the screws (36).

Figure 22:
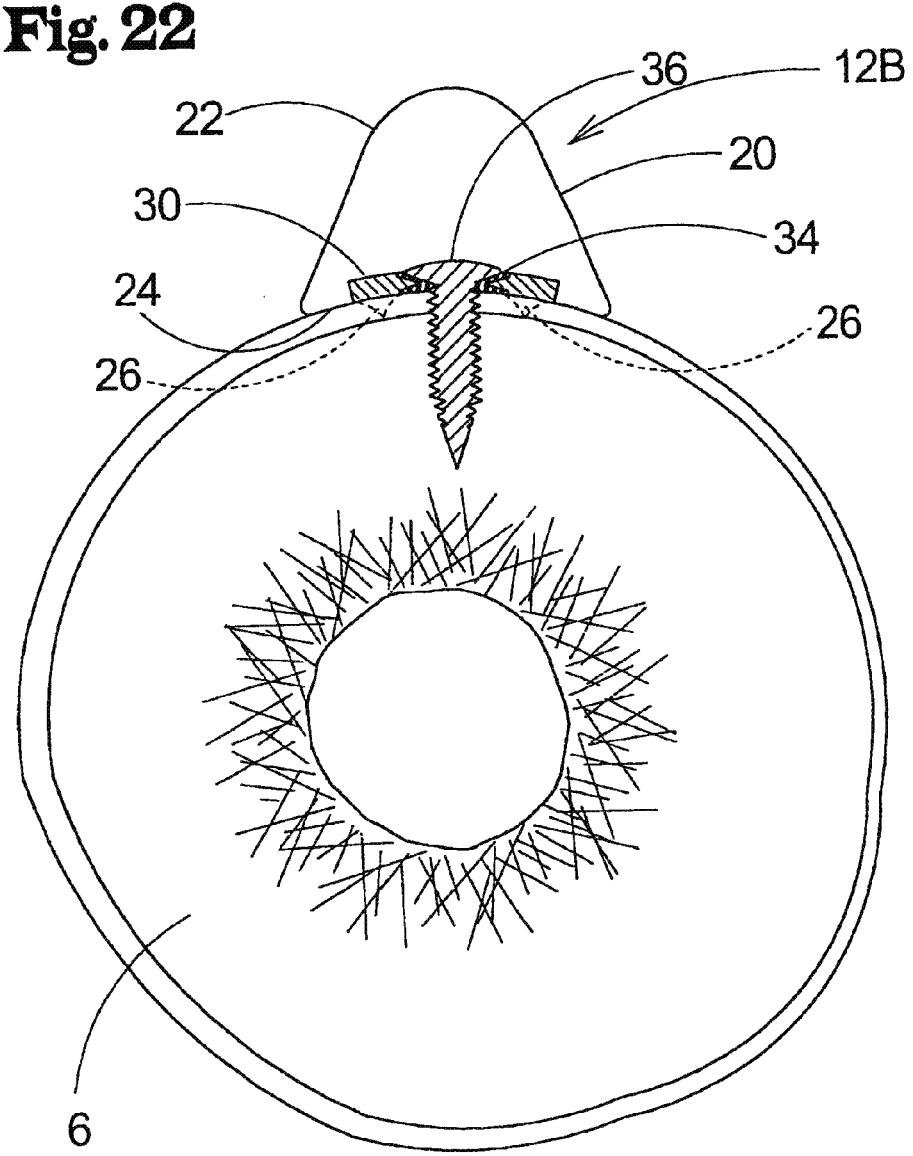
FIG. 22 is a schematic cross sectional view of the implant device 12B of FIG. 21 utilizing a screw method of mounting in accordance with an embodiment of the present invention.
Figure 24:
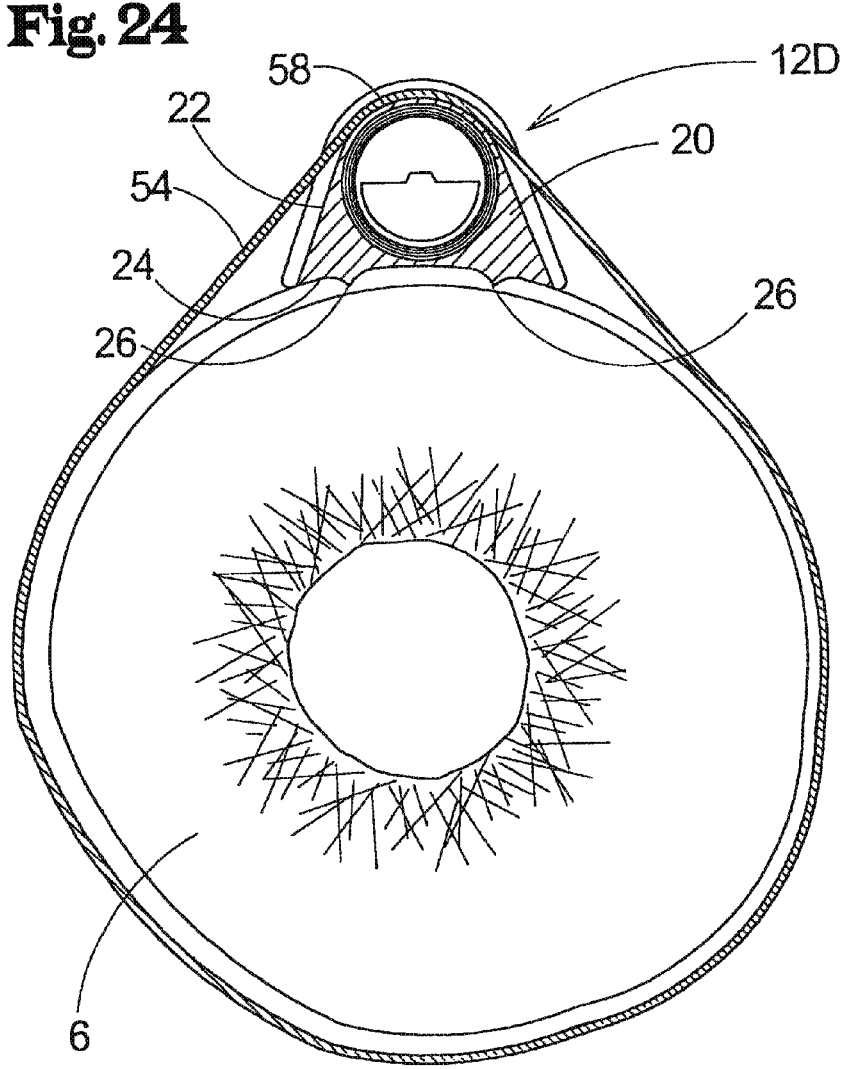
FIG. 24 is a schematic cross sectional view of the implant device 12D of FIG. 21 utilizing a band method mounting method in accordance with an embodiment of the present invention.

Implant device (12B) in FIG. 21 depicts an implant device similar to the embodiment depicted in FIGS. 12 through 14, which is illustratively shown attached to the bone tissue (6) of the fibula bone within the lower leg. The case (20) of the implant device (12) includes an engaging surface (24) which is contoured to substantially conform to the curved topography of the area of the fibula bone to which the implant device (12) is mounted. FIGS. 22 and 24 are cross sectional examples of the engaging surface (24) employed on the implant device (12B). The curved shape of the engaging surface (24) conforms to the curvature of the outer surface of the fibula where the implant device (12B) is attached. The engaging surface (24) includes a number of tines (26) to anchor the implant device (12) solidly to the bone tissue (6) and to transmit the vibrations generated by the implant device (12) to tissue in contact with the bone. In FIG. 22 the implant device (12B) may be additionally secured to the fibula by a pair of screws (36) which each pass through an aperture (32) of a flange (30) on the case (20) that forms a mount (28). A buffer (34) may be included between the aperture (32) and the screws (36) to help isolate the screws (36) from vibrations of the implant device (12B) that may loosen the screws (36) or damage the bone tissue (6) if transmitted without some degree of attenuation to the screws (36).

Figure 23:
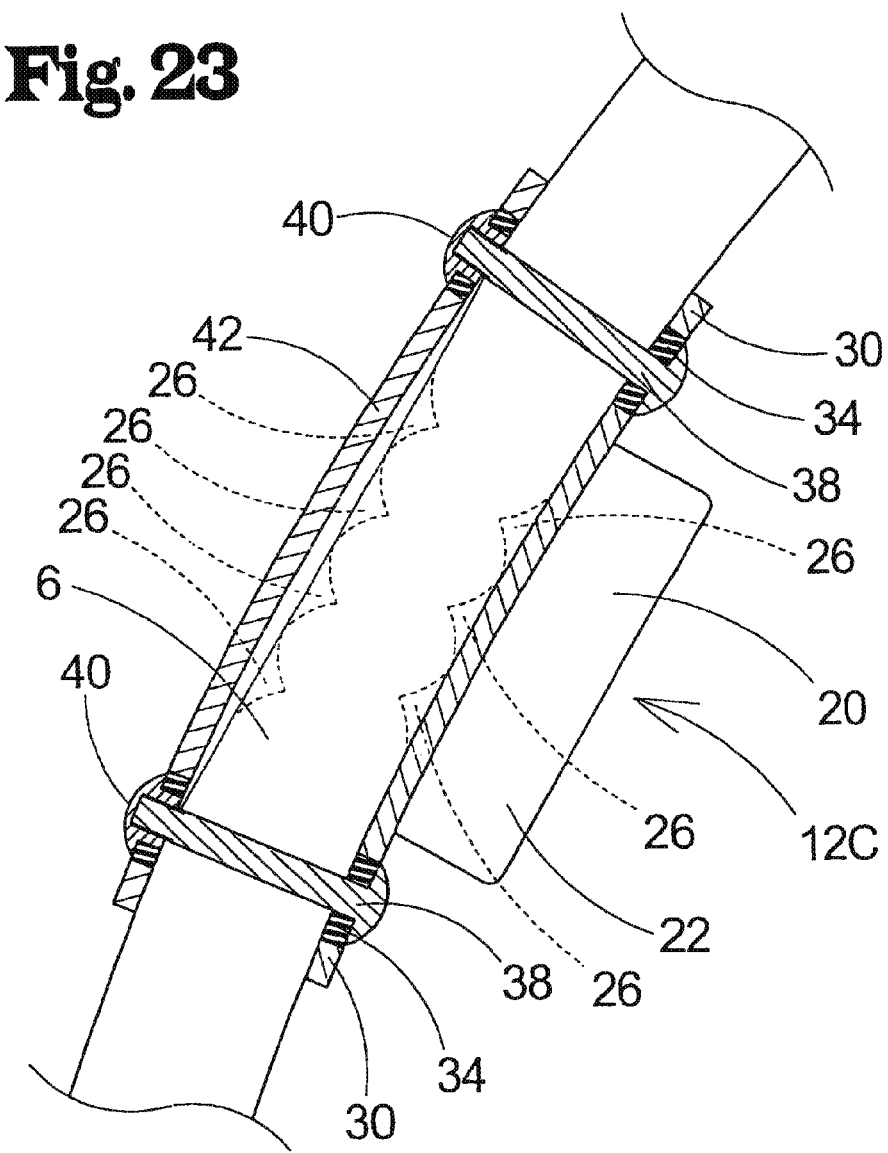
FIG. 23 is a schematic cross sectional view of the implant device 12C of FIG. 21 utilizing a back plate mounting method according to an embodiment of the present invention.

Implant device (12C) in FIG. 21 shows an implant device similar to the embodiment depicted in FIGS. 5 through 7, which is illustratively shown attached to the bone tissue (6) of the ilium of the pelvic bone or flange of the hip bone. The case (20) of the implant device (12C) includes an engaging surface (24) which is contoured to substantially conform to the topography of the area of the pelvis bone to which the implant device (12) is attached. FIG. 23 is a cross section of an example of the mounting structure employed in the implant device (12C). The curved shape of the engaging surface (24) may be contoured to substantially conform to the curvature of the pelvic bone to which the implant device (12C) is attached. The engaging surface (24) includes a number of tines (26) to anchor the implant device (12) substantially solidly to the bone tissue (6) and to transmit the vibrations generated by the implant device (12) to tissue in contact with the bone. The implant device (12C) may be additionally secured to the hip bone by a number of threaded fasteners such as bolts (38) which pass through an aperture (32) of a flange (30) of the case (20) that form a mount (28). A buffer (34) may be included between the aperture (32) and the bolts (38) to attenuate or isolate the bolts (38) from vibrations. FIG. 23 shows the bolts (38) passing through the bone tissue (6) and a plate (42) positioned on an opposite side of the bone tissue (6) and being engaged by a nut (40) bearing against the plate (42). The nuts (40) may have a locking capability to resist the loosening that is often produced by exposure to vibration. Optionally, the use of the nuts (40) may be eliminated by attaching the bolt (38) directly to the plate (42), such as by threading the aperture in the plate. The plate (42) may include an engaging surface (24) that is similar to the exterior (22) of the case (20) of the implant device (12) which may be contoured to conform to the topology of the bone to which it contacts. The plate (42) may also include a number of tines (26) to anchor the implant device (12) substantially solidly to the bone tissue (6) and to help transmit the vibrations generated by the implant device (12) to tissue in contact with the bone. Optionally, a buffer (34) may be included on the engaging surface (24) of the plate (42) to isolate the bolts (38) from vibrations of the implant device (12C).

Implant device (12D) in FIG. 21 shows an implant device similar to the embodiment depicted in FIGS. 12 through 14, which is illustratively shown attached to the bone tissue (6) of the femur bone within the upper leg. The case (20) of the implant device (12) includes an engaging surface (24) which is contoured to substantially conform to the curved topography of the surface of the area of the femur to which the implant device (12) is attached. FIGS. 22 and 24 are cross sectional examples of the engaging surface (24) employed by the implant device (12D). The curved shape of the engaging surface (24) may thus substantially conform to the curvature of the femur where the implant device (12D) is attached. The engaging surface (24) includes a number of tines (26) to anchor the implant device (12) substantially solidly to the bone tissue (6) and to transmit the vibrations generated by the implant device (12) to tissue in contact with the bone. In FIG. 24, the implant device (12D) is shown secured to the femur by a band (54) which encompasses the outer circumference of a section of the femur. The band (54) may engage the implant device (12) by nesting within a groove (58) formed on a portion of the exterior (22) of the case (20) of the implant device (12D). The band (54) may comprise a relatively inflexible or even rigid material such as metal, hard plastic, or inflexible fibers to provide a substantially unyielding attachment or may comprise materials which have flexible or even elastic qualities. The band (54) may also include a mechanism for attaching one end of the band (54) to the other end of the band (54), in some examples in an adjustable manner. The attachment mechanism may include, for example, a tension coupler, hinge pin, toothed grips, stitching, heat or sonic welds, an adhesive bond, a buckle, a hook and loop connector, and the like.

Implant device (12E) in FIG. 21 shows an implant device similar to the embodiment depicted in FIGS. 8 through 11, which is illustratively shown attached within the muscle tissue (4) of the quadriceps femoris within the upper leg. The implant device (12E) includes a mesh (48) mount (28) which is connected to the muscle tissue (4) of the quadriceps with sutures (50). Optionally, staples (52) may be used as a mounting element (98). Implant device (12) employing a mesh (48) for the mount (28) that is implanted among the fibers within a muscle bundle may not require any additional mounting elements (98). The natural healing process of the body of the patient may produce muscle tissue (4) that grows through the holes in the mesh (48) and may thus provide sufficient support to keep the implant device (12) in place. It is anticipated that in implementations where the implant device (12) is positioned within the fibers of a muscle bundle that a conforming engaging surface (24) (or optionally no mounting structure at all) may be sufficient to keep the implant device (12) in place.

Implant device (12F) in FIG. 21 shows an implant device similar to the embodiment depicted in FIGS. 8 through 11, which is illustratively shown attached to both the deep fascia (5) of a muscle bundle and bone tissue (6) using a mesh (48) as a mounting structure. An implant device (12) may be similarly attached to any type of bodily tissue, or combination of types of bodily tissues such as, for example, organ tissue, cartilage, dermal tissue, tendons (7), ligaments, teeth, arteries, veins, glands, lymph nodes, nerve tissue, brain tissue, fat, superficial fascia, etc.

Figure 17:
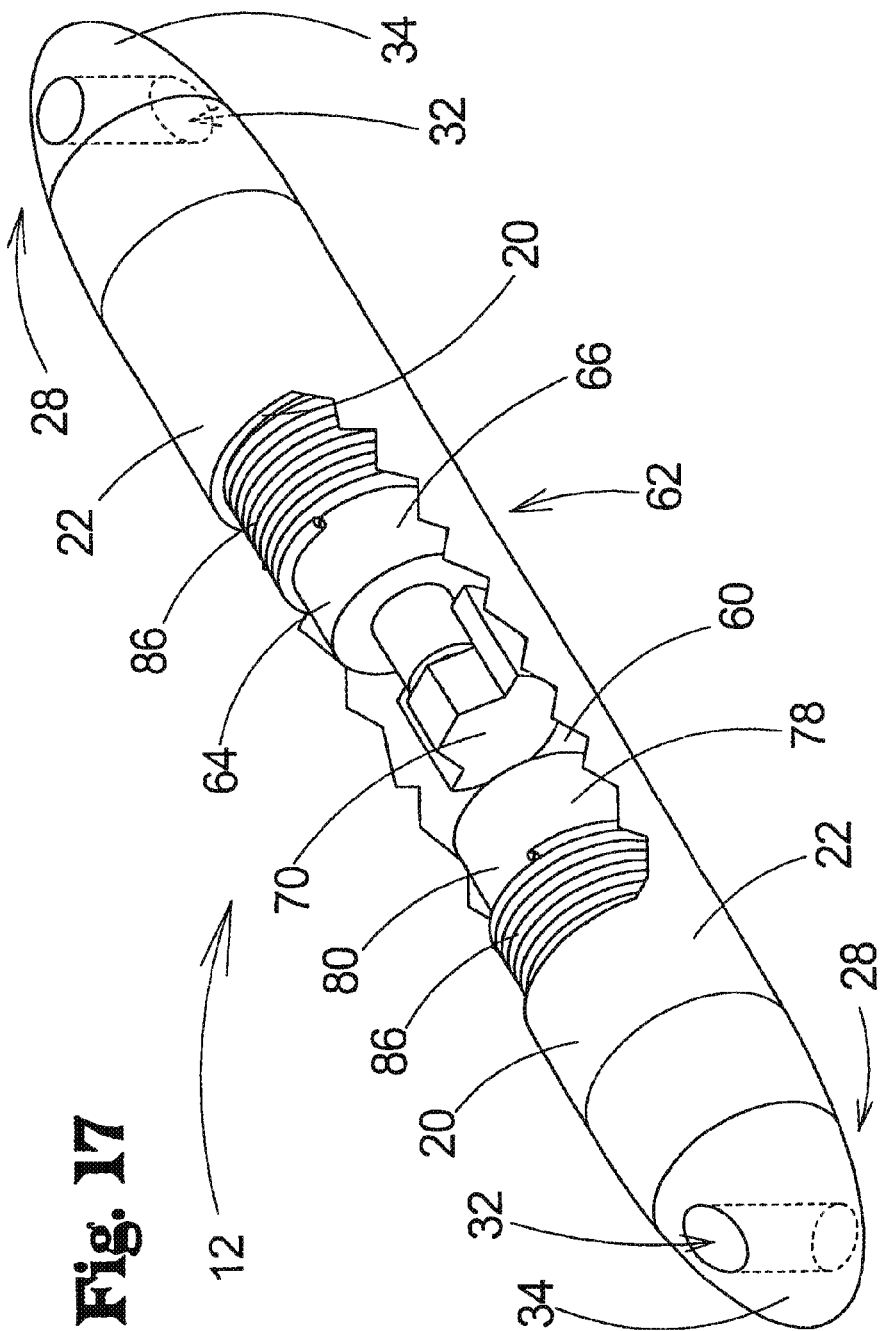
FIG. 17 is a schematic exploded view of the implant device of FIG. 15 in accordance to an embodiment of the present invention.

Implant device (12G) in FIG. 21 shows an implant device similar to the embodiment depicted in FIGS. 15 through 17, which includes a pair of lines (44) that are attached to the implant device (12G) through the apertures (32) mounted on either end of the case (20). The ends of the lines (44) located opposite the ends of the lines (44) that are connected to the implant device (12G) may form loops (46) that encircle the entire tendon (7) or a portion of the tendons (7) at either end of the muscle bundle. In this embodiment, the implant device (12) may be located outside the deep fascia (5) on the outside of the muscle or may be located amongst the muscle fibers inside the deep fascia (5).

Implant device (12H) of FIG. 21 shows an implant device (12) with a generally flat shape which employs both meshes (48) and a line (44) and loop (46) to secure the implant device (12H) to the deep fascia (5) of a muscle bundle and to the tendon (7) respectively.

The mounting structure for implant device (12I) shown in FIG. 21 is similar to the mounting structure used for implant device (12G), but also includes a third line (44) that is attached to apertures (32) at both ends of the implant device (12I) and encircles the muscle bundle or a portion thereof forming a loop (46). Any of the lines (44) may be further anchored to the deep fascia (5) of the muscle tissue (4) through the use of supplementary mounting elements (98) such as, for example, sutures (50), staples (52), mesh (48), adhesives, and the like.

Implant device (12J) shown in FIG. 21 shows an implant device (12) similar to the embodiment depicted in FIGS. 5 through 7, which includes a plurality of lines (44) attached to apertures (32) in a flange (30) of the case (20) forming mounts (28). Portions of the various lines (44) are shown connected to the deep fascia (5) through the use of, for example, sutures (50) and staples (52).

Figure 25:
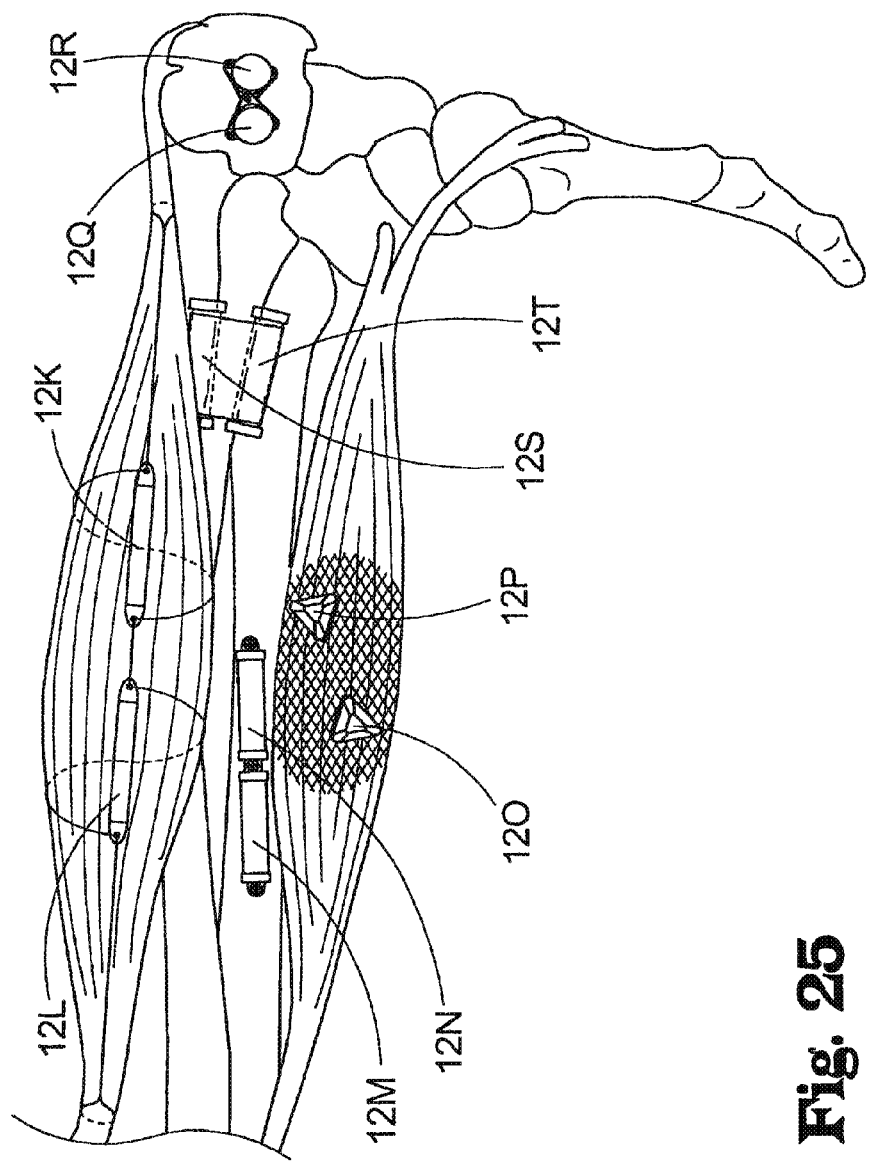
FIG. 25 is a schematic anatomically exploded view of a leg illustrating various methods of mounting multiple implant devices according to one or more embodiments of the present invention.
Figure 29:
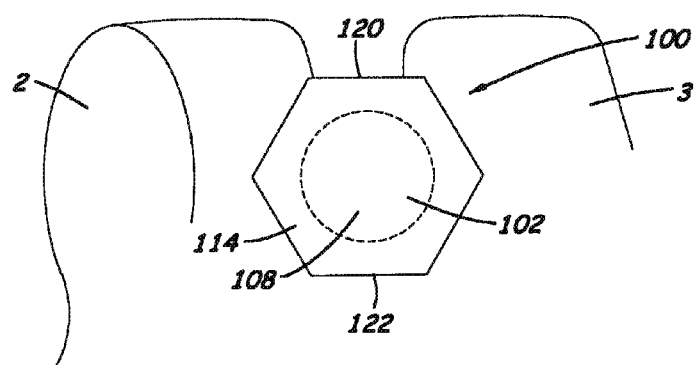
FIG. 29 is a schematic axial view of adjacent spinous processes with an embodiment of an implant device similar to that shown in FIG. 26 mounted on the processes.
Figure 30:
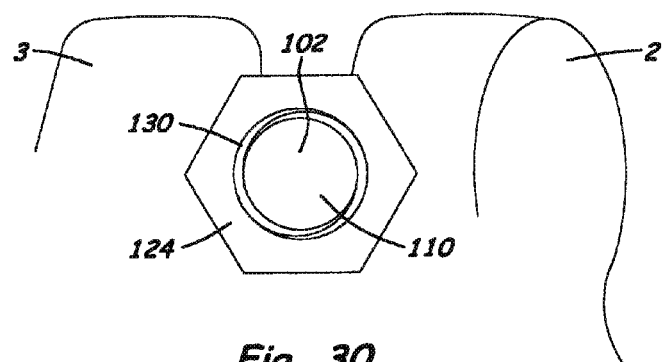
FIG. 30 is another schematic axial view of adjacent spinous processes from a vantage point opposite of the axial view of FIG. 29 with the implant device of FIG. 26 mounted thereon.
Figure 31:
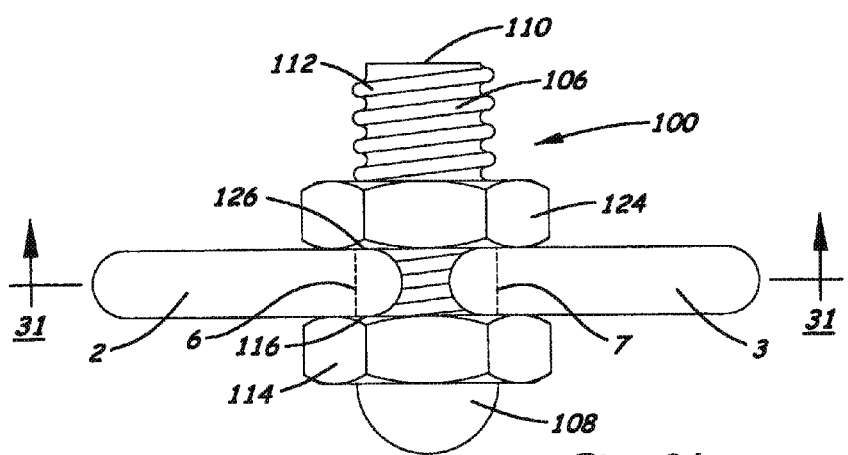
FIG. 31 is a schematic posterior view of adjacent spinous processes with the implant device of FIG. 26 mounted thereon.

FIG. 25 illustrates various structures for mounting more than one implant device (12) utilizing mounting elements (98). Implant device (12K) and implant device (12L) employ a mounting structure similar to those of implant device (12G) and implant device (12I) of FIG. 21, but are attached to each other in a tandem arrangement with a member (such as a line (44)) connecting implant device (12K) and implant device (12L) through the apertures (32).

Implant device (12M) and implant device (12N) of FIG. 25 employ a mounting structure that is similar to that of implant device (12B) of FIG. 21 but share a single screw (36) that passes through one aperture (32) of each of the implant devices (12M & N).

Implant device (12O) and implant device (12P) in FIG. 25 employ a mounting structure similar to that of implant device (12E) and implant device (12F) of FIG. 21 but are connected to one another by a mesh (48).

Implant device (12Q) and implant device (12R) in FIG. 25 employ a mounting structure similar to that of implant device (12A) in FIG. 21 but also similar to implant device (12M) and implant device (12N), these implant devices share a single screw (36) that passes through one aperture (32) of each of the implant device (12M) and implant device (12N).

Implant device (12Q) and implant device (12R) in FIG. 25 employ a mounting structure similar to that of implant device (12D) of FIG. 21, but these implant devices share a single band (54) that engages the grooves (58) in the exterior (22) of the case (20) of implant device (12Q) and implant device (12R).

It is anticipated that a plurality of implant devices (12) may be attached to a single plate (42) either directly or through a fastener or fasteners, and that a single clamp (56) may be utilized to anchor multiple implant devices (12).

Another aspect of the invention, involves a method of relieving pain or other conditions of a patient by imparting or applying a vibratory massage to tissue of the body of the patient, and most suitably tissue within the body of the patient. The method may include providing or obtaining an implant device (12) with features or elements such as those that have been described in this specification. The method may also include identifying tissue within the body of the patient that is suitable or desirable for the application of vibratory massage, such as, for example, tissue that is a source of discomfort or has suffered an injury. For the purposes of this description, the tissue to be treated will be referred to as the identified tissue. The condition or injury to the tissue of the patient may or may not be the cause for a pain condition in the patient. In other situations, the condition of the identified tissue may simply be of the type that is capable of benefiting from the application of vibratory massage.

The method may further include implanting the implant device (12) within the body of the patient. This aspect of the method may further include surgically opening the body of the patient such as by creating an incision in the tissue of the body of the patient to a location within the body of the patient at which the implant device (12) is to be located. This aspect may also include positioning the implant device (12) in the body of the patient in a manner such that the implant device is capable of transferring vibration by the implant device (12) to the identified tissue of the body of the patient. This aspect may also include placing the implant device (12) in contact with the identified tissue, and possibly mounting the implant device (12) on the identified tissue. Optionally, this aspect of the method may include mounting the implant device (12) on tissue (other than the identified tissue) that contacts the identified tissue, so that vibrations are transferred through the tissue to the identified tissue. In one illustrative and useful aspect of the method, the implant device (12) is positioned between two spinal processes of adjacent vertebrae of the patient, and the implant device is mounted to the spinal processes of those adjacent vertebrae. Another aspect of the method may be closing the opening in the body of the patient so that the implant device is contained within the body of the patient, which thus would prevent or eliminate any physical connection from the implant device to any device exterior of the body of the patient.

The method may additionally include causing vibration of the implant device within the body of the patient after implantation to thereby vibrate the identified tissue, and may further include sending instructions to the implant device to instruct it to vibrate. The method may include adjusting a frequency of the vibration of the implant device, and may include adjusting an amplitude of the vibration of the implant device. The method may include terminating the vibration of the implant device, and may also include resuming the vibration of the implant device after the vibration has been previously terminated.

In other embodiments of the invention, such as are illustratively shown in FIGS. 26 through 33, an implant device (100) has a case (102) with another adaptation that facilitates the mounting of the device on the patient, and also facilitates the transmission of the vibrations of the case to the tissue. In these embodiments, contours on the exterior surface (104) of the case (102) help to secure and anchor the case on the tissue of the body of the patient. These contours in the surface (104) may illustratively form a tissue engaging structure (106) that facilitate the mounting the device (100) on tissue. In more detail, the case (102) forms at least a portion of an exterior of the implant device (100) and defines an interior of the implant device as described above. The exterior surface (104) of the case (102) may be is configured to secure the case on a particular type of tissue of the body of the patient. Illustratively, the tissue of the patient may be at least one bone of the patient, and in the illustrative embodiments the tissue comprises a spinous process (2) of at least one vertebra 4 of the spine of the patient. The tissue may comprise the spinous processes (2, 3) of two adjacent vertebrae (4, 5). The case (102) may be elongated with a longitudinal axis A, and a first end (108) and a second end (110). The exterior surface (104) of the case (102) may also have a generally cylindrical shape.

The tissue engaging structure (106) on the exterior surface (104) may be configured to secure the case on tissue of the body of the patient. The tissue engaging structure (106) may include at least one helical ridge (112) formed on the exterior surface (104) of the case (102) and extending in a helical configuration about the circumference of the generally cylindrical exterior surface (104). The helical ridge (112) may extend from the second end (110) of the case (102) toward the first end (108) of the case. The helical ridge (112) may form a screw thread-like element. Optionally, the helical ridge (112) may be configured to cut threads or thread-receiving grooves into the patient's tissue, such as the bone of a spinous process.

Figure 32:
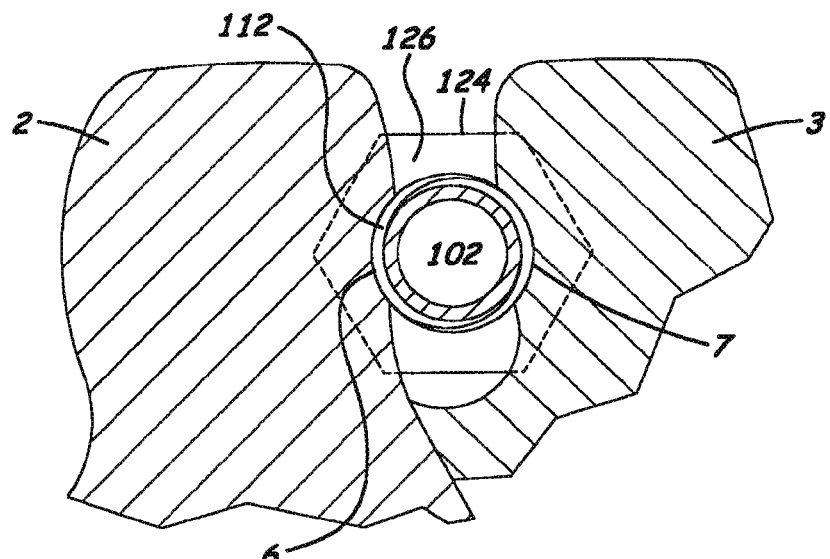
FIG. 32 is a schematic sectional view of adjacent spinous processes with the implant device of FIG. 26 mounted thereon, taken along line 31 of FIG. 31.
Figure 33:
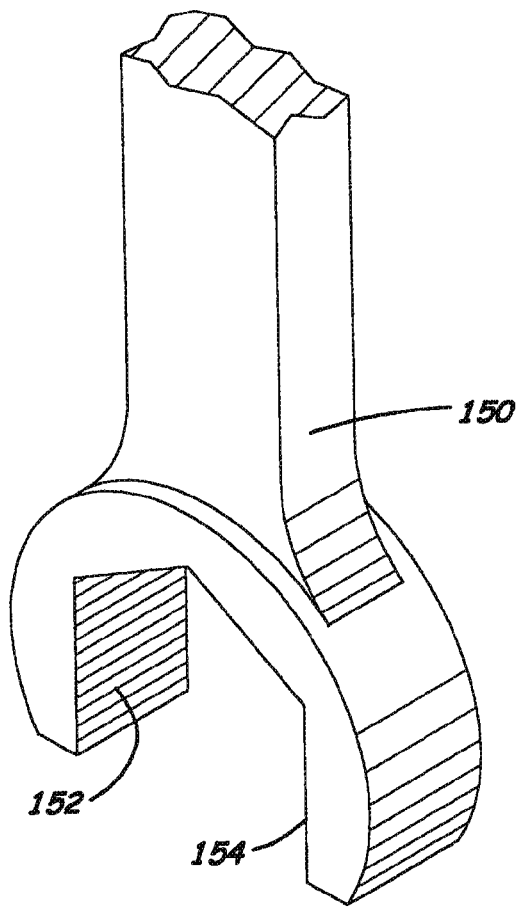
FIG. 33 is a schematic perspective view of a tool suitable for engaging the tool engaging structure of the bearing structure of FIG. 27.

A first bearing structure (114) may be formed by or mounted on the case (102) and may form or provide a first bearing surface (116) for bearing against the tissue of the patient, such as the bone of the spinous process, to facilitate and enhance the transmission of the vibration to the spinous processes. The first bearing structure (114) may be located toward the first end (108) of the case (102). The first bearing structure (114) may be integrally formed with the case (102), or may be mountable on the case by bonding on the case or rotation on the threads. The first bearing surface (114) may extend in a plane that is oriented substantially perpendicular to the longitudinal axis A of the case. The ridge (112) may extend from the second end (110) of the case toward and substantially to the first bearing surface (116). The first bearing structure (114) may include a tool engaging structure (118) that is configured to be engaged by a tool. The tool engaging structure (118) comprises at least two flat surfaces (120, 122) on the first bearing structure that may be located on substantially opposite sides of the first end (108) of the case. The tool engaging structure (118) may include three pairs of opposite surfaces arranged in a hexagonal configuration in a manner similar to the hexagonal head of a fastener to facilitate the ability of a took to engage opposite surfaces of the tool engaging structure in a confined surgical space regardless of the orientation of the structure (118). As illustrated in FIG. 32, one tool (150) which is suitable for engaging the opposite surfaces of the tool engaging structure (118) includes a pair of opposed faces (152, 154) for abutting the at least two flat surfaces (120, 122) of the tool engaging structure.

A bearing member (124) may be mountable on the case (102), and may have a second bearing surface (126) for bearing against the bone tissue of the patient, such as the aforementioned spinous processes of the adjacent vertebrae, to facilitate the transmission of case vibration to the tissue. The second bearing surface (126) may extend in a plane oriented substantially perpendicular to the longitudinal axis of the case when the bearing member (124) is mounted on the case. The bearing member (124) may be configured to be removable from the case once the member (124) is mounted on the case (102), although it should be recognized that the bearing member and case contour may be configured in a way that permits mounting of the bearing member on the case, but does not permit removal of the bearing member once it is mounted on the case.

Illustratively, the bearing member (124) may be configured to engage the ridge (112) of the tissue engaging structure (106). The bearing member (124) may have an aperture (126) therein through which a portion of the case (102) may be passed. The aperture (126) may be defined by an aperture surface (130) on the bearing member (124). The aperture surface (130) may be generally cylindrical in shape. The aperture surface (126) may include at least one helical groove (132) which may be complementary to the helical ridge (112) of the exterior surface of the case (102) such that rotation of the bearing member (124) with respect to the case in a first rotational direction moves the bearing member onto and along the case in a first longitudinal direction, and conversely rotation of the bearing member with respect to case in a second rotational direction moves the bearing member along the case in a second longitudinal direction and off of the case.

The contouring of the exterior surface, such as the helical ridge (112), may function not only to engage the tissue to anchor the case (102) to the tissue, but also to removably mount the bearing member (124) to the case during implantation of the case. Rotation of the bearing member (124) on the helical ridge (112) of the case (102) causes the bearing member to press the second bearing surface (126) against the tissue, and helps press the tissue against the first bearing surface (116).

The embodiments of the device (100) may be utilized in a space between spinous processes and that may partially extend into the processes to enhance the securement of the device as well as enhance the transmission of the vibration to the vertebrae of the spine. Further, the positioning of the case of the device (100) between the spinous processes may function to help immobilize the spinous processes and the corresponding vertebrae with respect to each other, and may also put the vertebrae in a flexed condition. One or both of the spinous processes (2, 3) between which the case (102) is to be mounted may have a portion removed to facilitate the mounting of the case therebetween.

In my copending patent application entitled "SURGICAL DRILL APPARATUS", U.S. patent application Ser. No. 12/326,580, filed Dec. 2, 2008, which is incorporated herein by reference in its entirety, a surgical drill device and a technique of forming a space between the spinous processes is disclosed that is suitable for receiving the case (102). The use of the drill apparatus (or other suitable device) may remove arcuate bites (6, 7) out of the respective spinous processes (2, 3) to form a substantially circular or cylindrical space between the processes to receive the case (102). Optionally, but not critically, the approximate diameter size of the space may be less than the diameter size of the case (102). Illustratively, the case (102) may have a diameter size of approximately 1 cm to approximately 2 cm, and the diameter size of the space formed between the spinous processes (2, 3) by the drill apparatus may be approximately 2 mm smaller than the diameter size of the case. The length of the case may be approximately 3 cm to approximately 4 cm. In one illustrative embodiment, the case has a length of approximately 3 cm and a diameter size of approximately 1 cm which is suitable for placement between the spinous processes of adjacent vertebrae of the spine.

It should be recognized that the vibratory implant device of the disclosure is useful for treating conditions other than pain as an analgesic. For example, the vibration produced by the implant device may be transmitted to various organs for the purpose of alleviating conditions in those organs or causing reactions by the organs. The vibrations may be administered in the manners described previously in this disclosure, and may be activated for periods of time to provide alleviate the condition being treated for those periods, or may be substantially constant without interruption.

Figure 34:
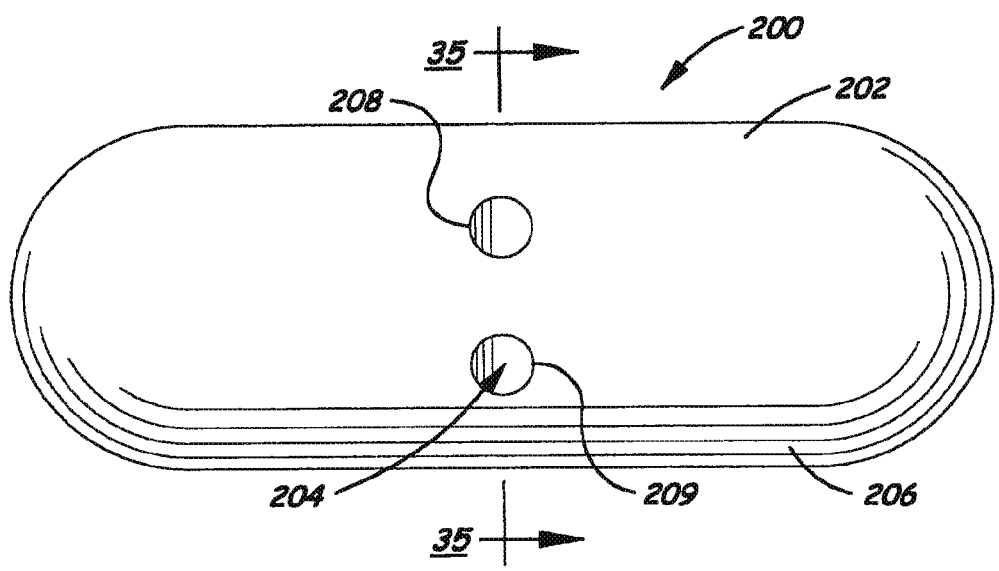
FIG. 34 is a schematic top view of another alternative implant device in accordance with an embodiment of the present invention.
Figure 35:
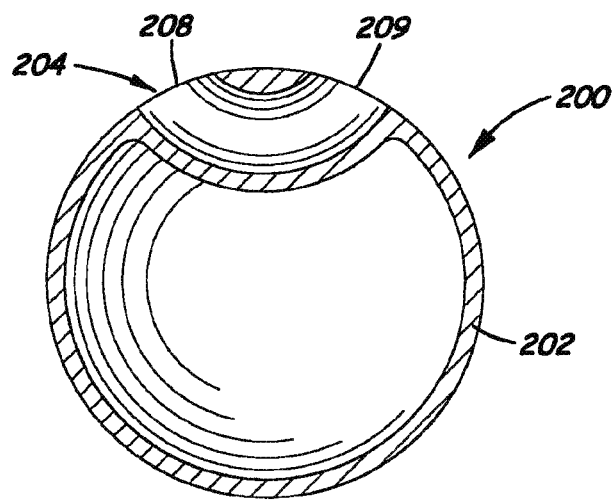
FIG. 35 is a schematic sectional view of the implant device of FIG. 34 taken along line 35 of FIG. 34 with components internal to the case being omitted for clarity.
Figure 36:
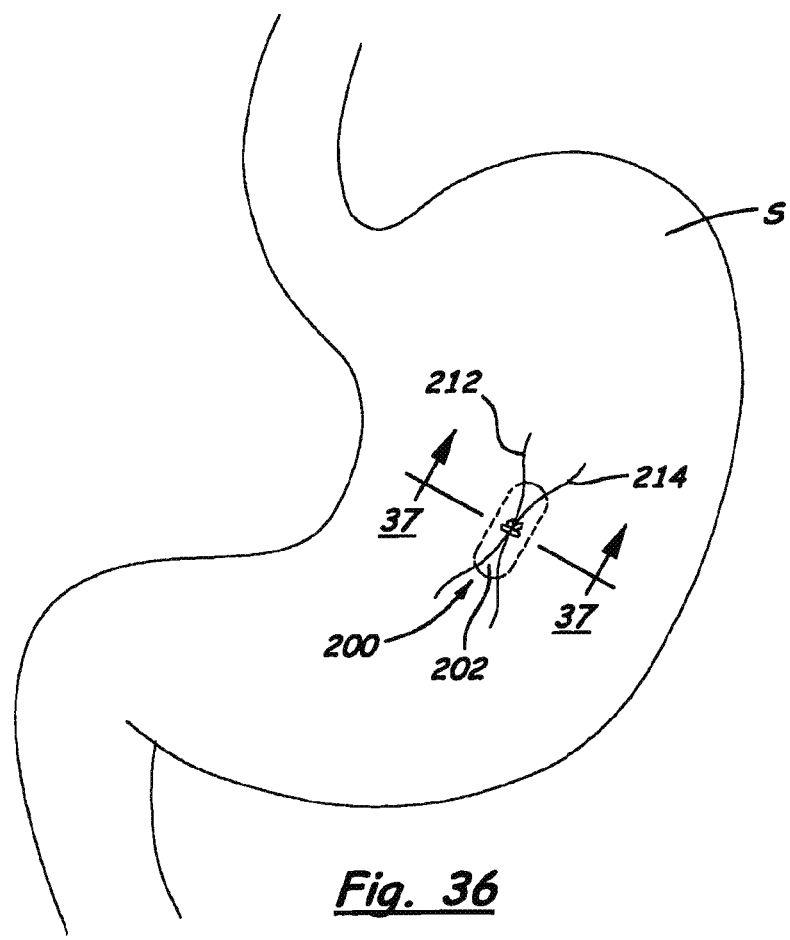
FIG. 36 is a schematic illustration of the implant device of FIG. 34 shown surgically secured to the wall of the stomach of a patient in accordance with an embodiment of the present invention.
Figure 37:
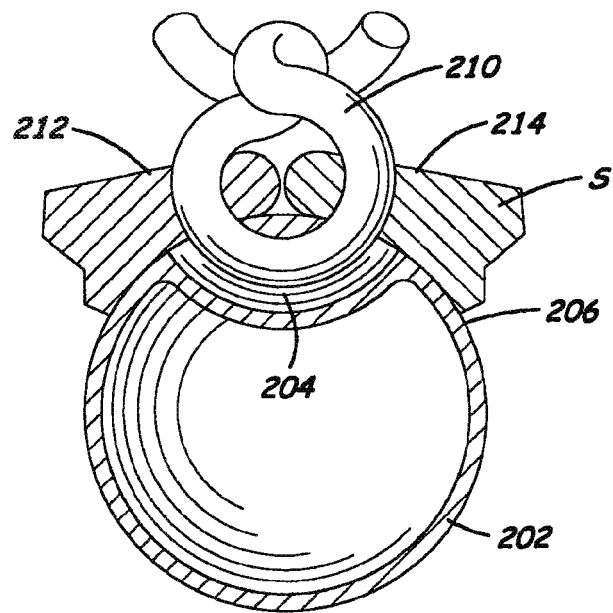
FIG. 37 is a schematic sectional view of the implant device of FIG. 34 taken along line 37 of FIG. 36.

In one exemplary application, the vibration of the implant device may be utilized to suppress the appetite of the patient for the ultimate purpose of causing or facilitating weight loss. The vibrations of the implant device may produce waves in the stomach tissue of the stomach wall that stimulate nerve fibers, (such as, for example, gastric distension mechanoreceptors) to help suppress appetite and cause a satiated feeling in the patient. Looking to FIGS. 34 through 37, one suitable configuration of the implant device is depicted in which the case (202) of the device (200) includes a passage (204) that extends though a portion of the exterior surface (206) of the case. The case (202) may be substantially cylindrical and may have ends that are rounded or semispherical, and the passage (204) may have openings (208, 209) that are basically located on the same side of the case (see FIGS. 34 and 35). The passage 204 is designed to receive a suture (210) or other securing member to hold or help hold the case (202) to the stomach S. As shown in FIGS. 36 and 37, a portion of the stomach S may be wrapped about the case (202) of the device (200) to thereby increase the area of contact between the exterior surface of the case and the exterior surface of the stomach. A suture (210) or other element may be used to attach the case to the stomach S. The suture (210) may be passed through the openings (208, 209) and the passage (204) of the case (202), and the suture (210) may be threaded through the spaced portions (212, 214) of the stomach wall to draw the portions of the stomach wall together about the case. By this technique, the case (202) is secured to the stomach S while the stomach is brought into more intimate and close contact with the exterior of the case.

Figure 38:
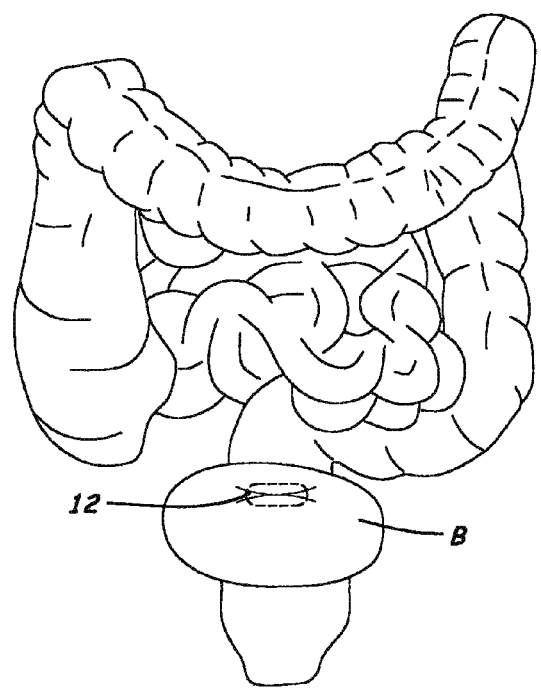
FIG. 38 is a schematic illustration of still another alternative embodiment of an implant device secured to the bladder of a patient in accordance with an embodiment of the present invention.

In another exemplary application of the implant device, the vibration produced by the device may be utilized to cause urination, or emptying of the bladder through normal channels, to treat bladder dysfunction or a urinary tract obstruction as well as ultimately prevent or reduce the occurrence of conditions such as bladder infection, diverticulum formation in the bladder, or bladder dilation when such dilation is undesirable, as well as other conditions of the bladder. The vibrations produced by the implant device (12) may stimulate the nerves that control the external sphincter and bladder functions to enhance the evacuation of the bladder. Looking to FIG. 38 of the drawings, the implant device (12) is shown positioned on a surface of the exterior of the bladder B. The device (12) may be positioned on a superior surface of the bladder B, and may be positioned between the locations on the bladder B where the ureters are joined to the bladder, although other positions for the device may be employed. The application of vibration to the bladder B may be periodic, or may be triggered by other factors such as detection that the bladder has filled with urine to a predetermined extent, as well as by patient activation.

Figure 39:
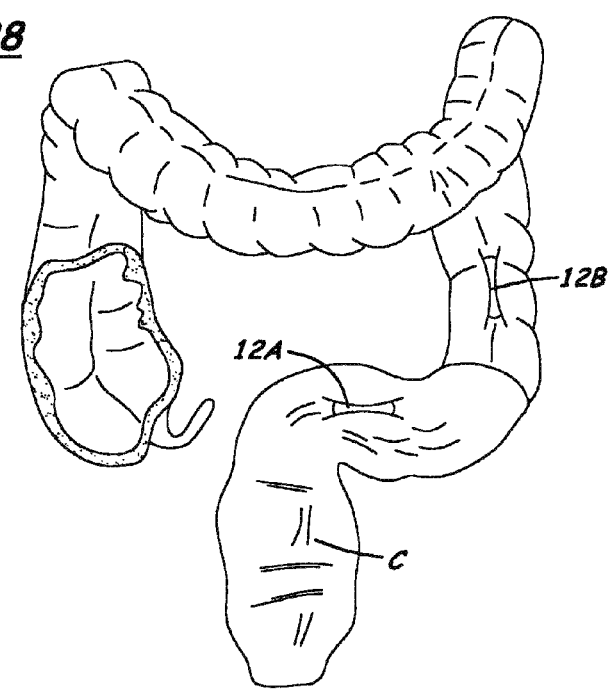
FIG. 39 is a schematic illustration of yet another alternative implant device device secured to the colon of a patient in accordance with an embodiment of the present invention.

In yet another exemplary application of the implant device, the vibration produced by the implant device may be employed to cause a bowel movement by transmitting vibration to various areas of the colon or large intestine, to ultimately resolve fecal impaction or constipation conditions, and a megacolon condition, as well as other conditions of the colon or bowel. Looking to FIG. 39 of the drawings, two possible positions or locations for the implant device (12) are illustrated. These positions of the implant device (12) may be used in the alternative, although two or more of the implant device (12) may be positioned to act on different or similar positions on the colon C. For example, for the conditions such as fecal impaction or constipation, positioning of the device on or adjacent to the sigmoid colon C, and particularly the mid-sigmoid colon, at or adjacent to the location of the device marked 12A, would be effective. As another example, for the condition of megacolon, positioning of the device on or adjacent to the descending colon, and particularly the mid-descending colon, at or adjacent to the location of the device marked 12B, would be effective particularly as this is an area where innervation is absent. The vibrations from the implant device stimulate nerve fibers in the wall of the colon to coordinate colonic wall movement and the advancement of stool along the colon.

In another exemplary application of the implant device, the vibration produced by the implant device may be employed to treat or minimize sexual dysfunction in male and female patients, although it should be recognized that the device may be employed where no dysfunction is present. For example, when utilized to treat sexual dysfunction in a female patient, the implant device (12) may be positioned internally in the suprapubic region of the abdomen (see FIG. 40), where the vibrations generated by the implant device may be transferred to the clitoral and vaginal nerve fibers to facilitate or cause a sensation of sexual pleasure. As another example, when used to treat sexual dysfunction in a male patient, the implant device may be positioned in the penis along the dorsal aspect region (see FIGS. 41A and 41B), where vibrations stimulate the penile nerve fibers to facilitate and increase blood flow in the penis and a stronger erection. Further, the positioning of the implant in the dorsal aspect region may allow vibrations from the implant device (12) in the penis to be transmitted to the clitoral region of the female partner during copulation. Although other positions within the penis may be employed, it is believed that the dorsal aspect portioning provides the greatest benefit to the patient.

It should be recognized that any manner disclosed herein for suitably securing the implant device to the organ to be affected, or a body structure adjacent or in communication with the organ to be affected, may be utilized, as well as other methods not set forth in this disclosure. Furthermore, the structure of the implant device (12) that is employed, including the configuration of the case, may be any suitable for securing the device and transmitting the vibration to the desired organ or tissue. In some of the methods of utilizing the implant device, the device is positioned on or against the exterior surface or integument of the organ to be affected, although it is possible that positions interior to the organ or tissue may be utilized.

It should be appreciated from the foregoing description and the many variations and options disclosed that, except when mutually exclusive, the features of the various embodiments described herein may be combined with features of other embodiments as desired while remaining within the intended scope of the disclosure.

It is to be understood that the above description is intended to be illustrative, and not restrictive. Many other embodiments and combinations of elements will be apparent to those skilled in the art upon reviewing the above description and accompanying drawings. The scope of the invention should, therefore, be determined with reference to the appended claims, along with the full scope of equivalents to which such claims are entitled.

What is claimed:

1. A method, comprising:
   placing an implant device near an exterior surface of a stomach, the implant device configured to produce and communicate a vibration to stomach tissue, the implant device including a case forming at least a portion of an exterior of the implant device and defining an interior of the implant device, a vibration generator mounted on the case and configured to vibrate the at least a portion of the exterior of the implant device, and a tissue engaging structure located on the exterior surface of the case and configured to engage the stomach tissue, the tissue engaging structure comprising a passage extending through a portion of the exterior surface of the case, the passage extending from an opening on a side of the case to another opening on substantially a same side of the case;

securing the implant device to the exterior surface of the stomach, including passing a suture through the passage and threading the suture through a wall of the stomach tissue; and activating the vibration generator of the implant device to cause the implant device to vibrate against the exterior surface of the stomach, wherein a vibration of the implant device against the exterior surface of the stomach is configured to stimulate a nerve to suppress an appetite.

2. The method of claim 1, wherein securing the implant device includes contacting an exterior of the case of the implant device with the exterior surface of the stomach.

3. The method of claim 1, wherein securing the implant device includes wrapping a portion of the stomach tissue about a portion of the case.

4. The method of claim 1, wherein securing the implant device includes mounting the implant device to the exterior surface of the stomach using a mounting structure formed integral to the case.

5. The method of claim 1, wherein the activating the vibration generator includes receiving a signal from a remote source using a signal receiver mounted on the case.

6. An implant device, comprising:
a case forming at least a portion of an exterior of the implant device and defining an interior of the implant device, the case comprising a passage extending from an opening on a side of the case, through a portion of the case, to another opening on the side of the case;
a vibration generator mounted on the case and configured to vibrate the at least a portion of the exterior of the implant device;
a power receiver comprising a receiving coil and configured to receive electrical energy from a remote source, the power receiver being disposed adjacent to the vibration generator; and
a tissue engaging structure located on the exterior surface of the case and configured to engage a stomach tissue, the tissue engaging structure comprising the passage configured to receive a suture.

7. The device of claim 6, wherein the vibration generator comprises an electrical motor.

8. The device of claim 6, wherein the vibration generator comprises a piezoelectric vibrator.

9. The device of claim 6, wherein the case has a substantially cylindrical shape.

10. The device of claim 6, wherein the case is formed of a biocompatible material.

11. The device of claim 6, wherein the implant device further comprises a power supply mounted on the case and configured to supply power to the vibration generator.

* * * * *